US012778452B2

(12) United States Patent
Lee et al.

(10) Patent No.: US 12,778,452 B2
(45) Date of Patent: Nov. 3, 2026

(54) ELECTRONIC DEVICE AND METHOD FOR DETECTING TREMOR IN ELECTRONIC DEVICE

(71) Applicant: Samsung Electronics Co., Ltd., Gyeonggi-do (KR)

(72) Inventors: Hongji Lee, Gyeonggi-do (KR); Jongmin Choi, Gyeonggi-do (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 568 days.

(21) Appl. No.: 17/896,504

(22) Filed: Aug. 26, 2022

(65) Prior Publication Data

US 2023/0074565 A1 Mar. 9, 2023

Related U.S. Application Data

(63) Continuation of application No. PCT/KR2022/006754, filed on May 11, 2022.

(30) Foreign Application Priority Data

Aug. 31, 2021 (KR) ........................ 10-2021-0115792

(51) Int. Cl.

*A61B 5/11* (2006.01)
*A61B 5/00* (2006.01)
*A61B 5/024* (2006.01)

(52) U.S. Cl.

CPC ........ *A61B 5/1101* (2013.01); *A61B 5/02433* (2013.01); *A61B 5/7264* (2013.01); (Continued)

(58) Field of Classification Search

CPC . A61B 5/1101; A61B 5/02433; A61B 5/7264; A61B 5/7282; A61B 5/742; A61B 2562/0219; A61B 5/7207

(Continued)

(56) References Cited

U.S. PATENT DOCUMENTS

2006/0094943 A1* 5/2006 Van Slyke ......... A61B 5/14551 600/323
2012/0179011 A1* 7/2012 Moon ...................... A61B 5/28 600/324

(Continued)

FOREIGN PATENT DOCUMENTS

CN 101365373 A 2/2009
CN 107157450 A 9/2017

(Continued)

OTHER PUBLICATIONS

International Search Report dated Aug. 22, 2022.

(Continued)

*Primary Examiner* — Devin B Henson
*Assistant Examiner* — Molly Halprin
(74) *Attorney, Agent, or Firm* — Sughrue Mion, PLLC

(57) ABSTRACT

In one embodiment, an electronic device may include a communication module, a display, a photoplethysmography (PPG) sensor, a motion sensor, a memory, and at least one processor. The at least one processor may be configured to obtain a first light signal and a second light signal sensed by the PPG sensor and three-axis acceleration signals sensed by the motion sensor, identify a tremorous state using the first light signal, the second light signal, and the three-axis acceleration signals, and display information indicating the tremorous state on the display. Other embodiments may also be possible.

16 Claims, 19 Drawing Sheets

(52) U.S. Cl.
CPC ............ *A61B 5/7282* (2013.01); *A61B 5/742* (2013.01); *A61B 2562/0219* (2013.01)

(58) Field of Classification Search
USPC .......................................................... 600/595
See application file for complete search history.

(56) References Cited

U.S. PATENT DOCUMENTS

| | | | | |
|---|---|---|---|---|
| 2013/0123684 | A1* | 5/2013 | Giuffrida | A61B 5/742 607/45 |
| 2015/0182160 | A1 | 7/2015 | Kim et al. | |
| 2017/0011210 | A1 | 1/2017 | Cheong et al. | |
| 2018/0196514 | A1 | 7/2018 | Allec et al. | |
| 2018/0353759 | A1 | 12/2018 | Starr et al. | |
| 2019/0015014 | A1 | 1/2019 | Lange | |
| 2019/0261890 | A1* | 8/2019 | Li | A61B 5/0816 |
| 2019/0286233 | A1 | 9/2019 | Newberry | |
| 2019/0365286 | A1* | 12/2019 | Powers, III | A61B 5/6828 |
| 2019/0374816 | A1 | 12/2019 | Yun et al. | |
| 2020/0025699 | A1 | 1/2020 | Yeo et al. | |
| 2020/0037942 | A1 | 2/2020 | Howard | |
| 2020/0093414 | A1 | 3/2020 | Na et al. | |
| 2020/0390367 | A1 | 12/2020 | Hall et al. | |
| 2020/0390403 | A1 | 12/2020 | Halperin et al. | |
| 2021/0145310 | A1* | 5/2021 | Lange | A61B 5/1455 |
| 2021/0212616 | A1 | 7/2021 | Honore et al. | |
| 2021/0248893 | A1 | 8/2021 | Van Dinther | |

FOREIGN PATENT DOCUMENTS

| | | | |
|---|---|---|---|
| CN | 110430802 | A | 11/2019 |
| CN | 113100756 | A | 7/2021 |
| KR | 10-2016-0037468 | A | 4/2016 |
| KR | 10-2017-0060893 | A | 6/2017 |
| KR | 10-2019-0138969 | A | 12/2019 |
| WO | 2020069219 | A1 | 4/2020 |

OTHER PUBLICATIONS

A Novel Non-parametric Approach of Tremor Detection Using Wrist-based Photoplethysmograph dated Jan. 1, 2021.
Motion Artifact Reduction for Wrist-worn Photoplethysmograph Sensors Based on Different Wavelengths dated Jan. 1, 2019.
Communication dated Apr. 17, 2026, issued by the Korean Ministry of Intellectual Property in Korean Patent Application No. 10-2021-0115792.
Communication dated Aug. 6, 2026 issued by the State Intellectual Property Office of People's Republic of China in Chinese Patent Application No. 202280059378.1.

* cited by examiner

ELECTRONIC DEVICE AND METHOD FOR DETECTING TREMOR IN ELECTRONIC DEVICE

CROSS-REFERENCE TO RELATED APPLICATION(S)

This application is a continuation application of, based on and claims priority under 35 U.S.C. § 120 to PCT International Application No. PCT/KR2022/006754, which was filed on May 11, 2022, and claims priority to Korean Patent Application No. 10-2021-0115792, filed on Aug. 31, 2021, in the Korean Intellectual Property Office, the disclosures of which are incorporated by reference herein their entireties.

BACKGROUND

Technical Field

One or more embodiments of the instant disclosure generally relate to technology for detecting a tremor in an electronic device.

Description of Related Art

Recent electronic devices come in various form factors for user convenience purposes and are reduced in size for easy portability. More interest is being paid to health, and so is technology capable of monitoring the health condition of users.

Electronic devices have been developed to measure and utilize various biometric signals and provide various services for the user's health care or monitoring of the user's health condition based on the biometric signals.

SUMMARY

With the development of technology, various different sensors can be equipped in electronic devices to measure biometric signals, and various attempts are being made to detect various symptoms related to the user's health using biometric signals.

One example of the user's health-related symptoms is tremor (or shake). A tremor may be involuntary vibrational motion that occurs regularly at a constant frequency in one or several parts of the body. Tremors may be a symptom of a number of diseases in that it is an involuntary movement. For example, a tremor itself may be a critical factor in diagnosing Parkinson's disease as being a representative symptom of Parkinson's patients.

In general, tremor may be subjectively identified (or diagnosed) by observation by a medical professional, such as a doctor or a clinician or may be identified (or detected) through a separate tremor detection device. However, diagnosis by a medical professional may be inconvenient in that the user needs to visit the medical professional, and use of a separate tremor detection device suffers from low accuracy in tremor detection because it conventionally uses accelerometer signals.

According to an embodiment of the disclosure, an electronic device may comprise a communication module, a display, a PPG sensor, a motion sensor, a memory, and at least one processor. The at least one processor may be configured to obtain a first light signal and a second light signal sensed by the PPG sensor and three-axis acceleration signals sensed by the motion sensor, identify a tremorous state using the first light signal, the second light signal, and the three-axis acceleration signals, and display information indicating the tremorous state on the display.

Further, according to an embodiment of the disclosure, a method for detecting a tremor in an electronic device may comprise obtaining a first light signal and a second light signal sensed by a PPG sensor of the electronic device and three-axis acceleration signals sensed by a motion sensor of the electronic device, identifying a tremorous state using the first light signal, the second light signal, and the three-axis acceleration signals, and displaying information indicating the tremorous state on a display.

Further, according to an embodiment of the disclosure, there may be provided a non-volatile storage medium storing instruction configured to, when executed by electronic device, cause the electronic device to perform at least one operation. The at least one operation may comprise obtaining a first light signal and a second light signal sensed by a PPG sensor and three-axis acceleration signals sensed by a motion sensor, identifying a tremorous state using the first light signal, the second light signal, and the three-axis acceleration signals, and displaying information indicating the tremorous state on a display.

Additional aspects will be set forth in part in the description which follows and, in part, will be apparent from the description, or may be learned by practice of the presented embodiments.

BRIEF DESCRIPTION OF THE DRAWINGS

The above and other aspects, features, and advantages of certain embodiments of the present disclosure will be more apparent from the following description taken in conjunction with the accompanying drawings, in which.

The same or similar reference denotations may be used to refer to the same or similar elements throughout the specification and the drawings.

DETAILED DESCRIPTION

According to certain embodiments of the disclosure, there is provided an electronic device capable of more precisely detecting tremor using a photoplethysmography (PPG) sensor and an accelerometer. A method for detecting the tremor by the electronic device is also disclosed.

According to certain embodiments of the disclosure, there is provided an electronic device capable of identifying tremor, including the severity of the tremor, using a PPG sensor and an accelerometer. A method for detecting the tremor by the electronic device is also disclosed.

According to certain embodiments of the disclosure, the electronic device may more precisely provide information about whether a tremor is detected using a PPG sensor and an accelerometer.

According to certain embodiments of the disclosure, the electronic device may identify and provide the severity of the tremor upon detecting the tremor, thereby allowing the user to be aware how severe the tremor is.

According to certain embodiments of the disclosure, the electronic device may provide guide information associated with the tremor upon detecting the tremor, thereby allowing the user to easily treat the tremor.

Certain embodiments of the present disclosure are now described with reference to the accompanying drawings. As used herein, the term "user" may denote a human or another device using the electronic device. The terms as used herein are provided merely to describe some embodiments thereof, but not to limit the scope of other embodiments of the present disclosure. It is to be understood that the singular forms "a," "an," and "the" include plural references unless the context clearly dictates otherwise. All terms including technical and scientific terms used herein have the same meaning as commonly understood by one of ordinary skill in the art to which the embodiments of the present disclosure belong. It will be further understood that terms, such as those defined in commonly used dictionaries, should be interpreted as having a meaning that is consistent with their meaning in the context of the relevant art and will not be interpreted in an idealized or overly formal sense unless expressly so defined herein. In some cases, the terms defined herein may be interpreted to exclude embodiments of the present disclosure.

Figure 1:
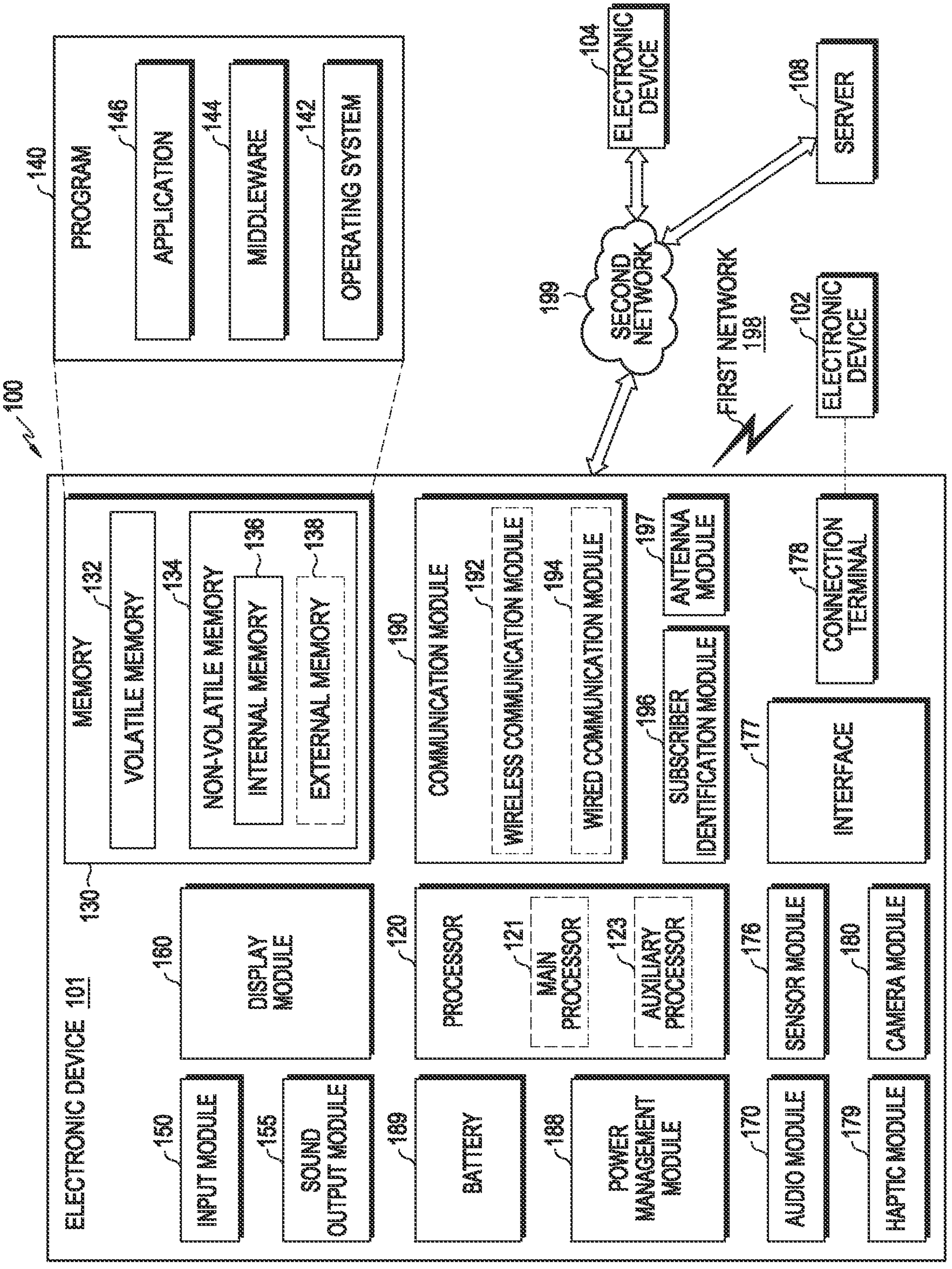
FIG. 1 is a block diagram illustrating an electronic device in a network environment according to an embodiment.

FIG. 1 is a block diagram illustrating an electronic device 101 in a network environment 100 according to an embodiment.

Referring to FIG. 1, the electronic device 101 in the network environment 100 may communicate with at least one of an electronic device 102 via a first network 198 (e.g., a short-range wireless communication network), or an electronic device 104 or a server 108 via a second network 199 (e.g., a long-range wireless communication network). According to an embodiment, the electronic device 101 may communicate with the electronic device 104 via the server 108. According to an embodiment, the electronic device 101 may include a processor 120, memory 130, an input module 150, a sound output module 155, a display module 160, an audio module 170, a sensor module 176, an interface 177, a connecting terminal 178, a haptic module 179, a camera module 180, a power management module 188, a battery 189, a communication module 190, a subscriber identification module (SIM) 196, or an antenna module 197. In some embodiments, at least one (e.g., the connecting terminal 178) of the components may be omitted from the electronic device 101, or one or more other components may be added in the electronic device 101. According to an embodiment, some (e.g., the sensor module 176, the camera module 180, or the antenna module 197) of the components may be integrated into a single component (e.g., the display module 160).

The processor 120 may execute, for example, software (e.g., a program 140) to control at least one other component (e.g., a hardware or software component) of the electronic device 101 coupled with the processor 120, and may perform various data processing or computation. According to one embodiment, as at least part of the data processing or computation, the processor 120 may store a command or data received from another component (e.g., the sensor module 176 or the communication module 190) in volatile memory 132, process the command or the data stored in the volatile memory 132, and store resulting data in non-volatile memory 134. According to an embodiment, the processor 120 may include a main processor 121 (e.g., a central processing unit (CPU) or an application processor (AP)), or an auxiliary processor 123 (e.g., a graphics processing unit (GPU), a neural processing unit (NPU), an image signal processor (ISP), a sensor hub processor, or a communication processor (CP)) that is operable independently from, or in conjunction with, the main processor 121. For example, when the electronic device 101 includes the main processor 121 and the auxiliary processor 123, the auxiliary processor 123 may be configured to use lower power than the main processor 121 or to be specified for a designated function. The auxiliary processor 123 may be implemented as separate from, or as part of the main processor 121.

The auxiliary processor 123 may control at least some of functions or states related to at least one component (e.g., the display module 160, the sensor module 176, or the communication module 190) among the components of the electronic device 101, instead of the main processor 121 while the main processor 121 is in an inactive (e.g., sleep) state, or together with the main processor 121 while the main processor 121 is in an active state (e.g., executing an application). According to an embodiment, the auxiliary processor 123 (e.g., an image signal processor or a communication processor) may be implemented as part of another component (e.g., the camera module 180 or the communication module 190) functionally related to the auxiliary processor 123. According to an embodiment, the auxiliary processor 123 (e.g., the neural processing unit) may include a hardware structure specified for artificial intelligence model processing. The artificial intelligence model may be generated via machine learning. Such learning may be performed, e.g., by the electronic device 101 where the artificial intelligence is performed or via a separate server (e.g., the server 108). Learning algorithms may include, but are not limited to, e.g., supervised learning, unsupervised learning, semi-supervised learning, or reinforcement learning. The artificial intelligence model may include a plurality of artificial neural network layers. The artificial neural network may be a deep neural network (DNN), a convolutional neural network (CNN), a recurrent neural network (RNN), a restricted Boltzmann machine (RBM), a deep belief network (DBN), a bidirectional recurrent deep neural network (BRDNN), deep Q-network or a combination of two or more thereof but is not limited thereto. The artificial intelligence model may, additionally or alternatively, include a software structure other than the hardware structure.

The memory 130 may store various data used by at least one component (e.g., the processor 120 or the sensor module 176) of the electronic device 101. The various data may include, for example, software (e.g., the program 140) and input data or output data for a command related thereto. The memory 130 may include the volatile memory 132 or the non-volatile memory 134.

The program 140 may be stored in the memory 130 as software, and may include, for example, an operating system (OS) 142, middleware 144, or an application 146.

The input module 150 may receive a command or data to be used by other component (e.g., the processor 120) of the electronic device 101, from the outside (e.g., a user) of the electronic device 101. The input module 150 may include, for example, a microphone, a mouse, a keyboard, keys (e.g., buttons), or a digital pen (e.g., a stylus pen).

The sound output module 155 may output sound signals to the outside of the electronic device 101. The sound output module 155 may include, for example, a speaker or a receiver. The speaker may be used for general purposes, such as playing multimedia or playing record. The receiver may be used for receiving incoming calls. According to an embodiment, the receiver may be implemented as separate from, or as part of the speaker.

The display module 160 may visually provide information to the outside (e.g., a user) of the electronic device 101. The display 160 may include, for example, a display, a hologram device, or a projector and control circuitry to control a corresponding one of the display, hologram device, and projector. According to an embodiment, the display 160 may include a touch sensor configured to detect a touch, or a pressure sensor configured to measure the intensity of a force generated by the touch.

The audio module 170 may convert a sound into an electrical signal and vice versa. According to an embodiment, the audio module 170 may obtain the sound via the input module 150, or output the sound via the sound output module 155 or a headphone of an external electronic device (e.g., an electronic device 102) directly (e.g., wiredly) or wirelessly coupled with the electronic device 101.

The sensor module 176 may detect an operational state (e.g., power or temperature) of the electronic device 101 or an environmental state (e.g., a state of a user) external to the electronic device 101, and then generate an electrical signal or data value corresponding to the detected state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols to be used for the electronic device 101 to be coupled with the external electronic device (e.g., the electronic device 102) directly (e.g., wiredly) or wirelessly. According to an embodiment, the interface 177 may include, for example, a high definition multimedia interface (HDMI), a universal serial bus (USB) interface, a secure digital (SD) card interface, or an audio interface.

A connecting terminal 178 may include a connector via which the electronic device 101 may be physically connected with the external electronic device (e.g., the electronic device 102). According to an embodiment, the connecting terminal 178 may include, for example, a HDMI connector, a USB connector, a SD card connector, or an audio connector (e.g., a headphone connector).

The haptic module 179 may convert an electrical signal into a mechanical stimulus (e.g., a vibration or motion) or electrical stimulus which may be recognized by a user via his tactile sensation or kinesthetic sensation. According to an embodiment, the haptic module 179 may include, for example, a motor, a piezoelectric element, or an electric stimulator.

The camera module 180 may capture a still image or moving images. According to an embodiment, the camera module 180 may include one or more lenses, image sensors, image signal processors, or flashes.

The power management module 188 may manage power supplied to the electronic device 101. According to one embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may support establishing a direct (e.g., wired) communication channel or a wireless communication channel between the electronic device 101 and the external electronic device (e.g., the electronic device 102, the electronic device 104, or the server 108) and performing communication via the established communication channel. The communication module 190 may include one or more communication processors that are operable independently from the processor 120 (e.g., the application processor (AP)) and supports a direct (e.g., wired) communication or a wireless communication. According to an embodiment, the communication module 190 may include a wireless communication module 192 (e.g., a cellular communication module, a short-range wireless communication module, or a global navigation satellite system (GNSS) communication module) or a wired communication module 194 (e.g., a local area network (LAN) communication module or a power line communication (PLC) module). A corresponding one of these communication modules may communicate with the external electronic device 104 via a first network 198 (e.g., a short-range communication network, such as Bluetooth™, wireless-fidelity (Wi-Fi) direct, or infrared data association (IrDA)) or a second network 199 (e.g., a long-range communication network, such as a legacy cellular network, a 5G network, a next-generation communication network, the Internet, or a computer network (e.g., local area network (LAN) or wide area network (WAN)). These various types of communication modules may be implemented as a single component (e.g., a single chip), or may be implemented as multi components (e.g., multi chips) separate from each other. The wireless communication module 192 may identify or authenticate the electronic device 101 in a communication network, such as the first network 198 or the second network 199, using subscriber information (e.g., international mobile subscriber identity (IMSI)) stored in the subscriber identification module 196.

The wireless communication module 192 may support a 5G network, after a 4G network, and next-generation communication technology, e.g., new radio (NR) access technology. The NR access technology may support enhanced mobile broadband (eMBB), massive machine type communications (mMTC), or ultra-reliable and low-latency communications (URLLC). The wireless communication module 192 may support a high-frequency band (e.g., the mmWave band) to achieve, e.g., a high data transmission rate. The wireless communication module 192 may support various technologies for securing performance on a high-frequency band, such as, e.g., beamforming, massive multiple-input and multiple-output (massive MIMO), full dimensional MIMO (FD-MIMO), array antenna, analog beam-forming, or large scale antenna. The wireless communication module 192 may support various requirements specified in the electronic device 101, an external electronic device (e.g., the electronic device 104), or a network system (e.g., the second network 199). According to an embodiment, the wireless communication module 192 may support a peak data rate (e.g., 20 Gbps or more) for implementing eMBB, loss coverage (e.g., 164 dB or less) for implementing mMTC, or U-plane latency (e.g., 0.5 ms or less for each of downlink (DL) and uplink (UL), or a round trip of 1 ms or less) for implementing URLLC.

The antenna module 197 may transmit or receive a signal or power to or from the outside (e.g., the external electronic device). According to an embodiment, the antenna module 197 may include one antenna including a radiator formed of a conductor or conductive pattern formed on a substrate (e.g., a printed circuit board (PCB)). According to an embodiment, the antenna module 197 may include a plurality of antennas (e.g., an antenna array). In this case, at least one antenna appropriate for a communication scheme used in a communication network, such as the first network 198 or the second network 199, may be selected from the plurality of antennas by, e.g., the communication module 190. The signal or the power may then be transmitted or received between the communication module 190 and the external electronic device via the selected at least one antenna. According to an embodiment, other parts (e.g., radio frequency integrated circuit (RFIC)) than the radiator may be further formed as part of the antenna module 197. According to various embodiments, the antenna module 197 may form a mmWave antenna module. According to an embodiment, the mmWave antenna module may include a printed circuit board, a RFIC disposed on a first surface (e.g., the bottom surface) of the printed circuit board, or adjacent to the first surface and capable of supporting a designated high-frequency band (e.g., the mmWave band), and a plurality of antennas (e.g., array antennas) disposed on a second surface (e.g., the top or a side surface) of the printed circuit board, or adjacent to the second surface and capable of transmitting or receiving signals of the designated high-frequency band.

At least some of the above-described components may be coupled mutually and communicate signals (e.g., commands or data) therebetween via an inter-peripheral communication scheme (e.g., a bus, general purpose input and output (GPIO), serial peripheral interface (SPI), or mobile industry processor interface (MIPI)).

According to an embodiment, commands or data may be transmitted or received between the electronic device 101 and the external electronic device 104 via the server 108 coupled with the second network 199. The external electronic devices 102 or 104 each may be a device of the same or a different type from the electronic device 101. According to an embodiment, all or some of operations to be executed at the electronic device 101 may be executed at one or more of the external electronic devices 102, 104, or 108. For example, if the electronic device 101 should perform a function or a service automatically, or in response to a request from a user or another device, the electronic device 101, instead of, or in addition to, executing the function or the service, may request the one or more external electronic devices to perform at least part of the function or the service. The one or more external electronic devices receiving the request may perform the at least part of the function or the service requested, or an additional function or an additional service related to the request, and transfer an outcome of the performing to the electronic device 101. The electronic device 101 may provide the outcome, with or without further processing of the outcome, as at least part of a reply to the request. To that end, a cloud computing, distributed computing, mobile edge computing (MEC), or client-server computing technology may be used, for example. The electronic device 101 may provide ultra low-latency services using, e.g., distributed computing or mobile edge computing. In another embodiment, the external electronic device 104 may include an Internet-of-things (IoT) device. The server 108 may be an intelligent server using machine learning and/or a neural network. According to an embodiment, the external electronic device 104 or the server 108 may be included in the second network 199. The electronic device 101 may be applied to intelligent services (e.g., smart home, smart city, smart car, or health-care) based on 5G communication technology or IoT-related technology.

Figure 2:
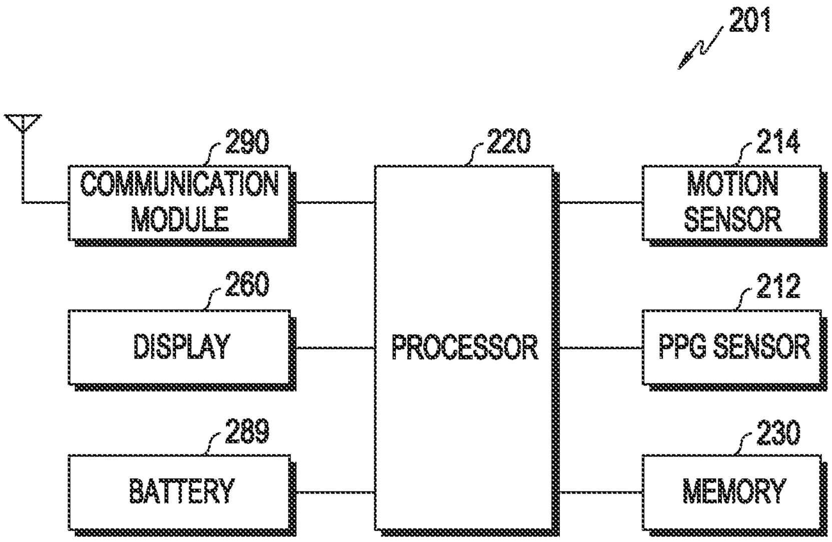
FIG. 2 is a block diagram illustrating a configuration of an electronic device according to an embodiment.

FIG. 2 is a block diagram illustrating an electronic device according to an embodiment.

Referring to FIG. 2, according to an embodiment, an electronic device 201 (e.g., the electronic device 101 of FIG. 1) may include a PPG sensor 212, a motion sensor 214, a processor (or at least one processor) 220, a memory 230, a display 260, a battery 289, and/or a communication module 290. The electronic device 201 is not limited thereto and may include more components or exclude some of the above-described components. According to an embodiment, the electronic device 201 may include the whole or part of the electronic device 101 of FIG. 1.

According to an embodiment, the PPG sensor (e.g., photoplethysmography sensor) 212 may measure changes in the volume of blood in the blood vessels by measuring the light transmittance using an optical sensor. This measurement is based on the characteristic that the volume of blood vessels is changed due to the blood flow in blood vessels changing as the heart repeatedly contracts and relaxes. According to an embodiment, the PPG sensor 212 may include at least one light emitting unit (or emitter (e.g., light emitting diode (LED))), at least one light receiving unit (or receiver (e.g., photodiode)), and a measuring unit. The light emitting unit may convert electrical energy into light energy, and the light receiving unit may convert light energy into electrical energy. The light output by at least one light emitting unit may include IR light and visible light (red light, blue light, and green light). If the light is transferred from at least one light emitting unit to the skin, part of the light is absorbed by the skin, and the rest is reflected and may be detected by at least one light receiving unit. When the PPG sensor 212 is in contact with the body, blood flow increases in blood vessels during the systole of the heart so that the amount of light detected through the light receiving unit decreases. During the diastole of the heart, the amount of light detected through the light receiving unit may increase due to a decrease in blood flow in the blood vessels. According to an embodiment, the measuring unit may process the signal according to the amount of reflected light, detected through the light receiving unit, thereby measuring various biometric aspects of the user such as blood pressure, blood sugar, heart rate, and/or blood volume.

According to an embodiment, the at least one light receiving unit may detect light of different wavelengths. For example, the at least one light receiving unit may detect the first wavelength of first light (e.g., IR light) and the second wavelength of second light (e.g., green light), respectively, which are reflected after partially absorbed by the body (e.g., skin), of the IR light and green light output by the at least one light emitting unit. For example, light having long wavelength that is equal to or longer than IR light may be absorbed by water in the cells, and light having short wavelength shorter than that of green light may be absorbed by the melanin component in the skin, so that the PPG sensor 212 may use the first wavelength of first light and the second wavelength of second light among the light having a wavelength range not more than (or less than) the IR wavelength and not less than the green light wavelength. For example, the first wavelength of first light may differ from the second wavelength of second light in the penetration depth based on the physical constitutional characteristics. For example, the first wavelength of first light may be light sensitive to dynamic noise (or motion) due to the penetration depth based on the physical constitutional characteristics as compared with the second wavelength of second light.

For example, the detected light signal may include a noise component due to the motion when the light detection operation is performed and, if light detection is performed when the motion occurs, the first light (IR light) signal may include more motion-induced noise components than the second light (green light) signal. According to an embodiment, the measuring unit may provide the processor 220 with a PPG signal including the first wavelength of first light signal (e.g., IR light signal) and second wavelength of second light signal (green light signal) detected from the at least one light receiving unit.

According to an embodiment, the motion sensor 214 may sense the motion of the electronic device 201 or the motion of the user wearing or carrying the electronic device 201. For example, the motion sensor 214 may include an accelerometer and may further include a gyroscope, a barometer, and/or a geomagnetic sensor. The acceleration sensor may sense acceleration or impact caused by the motion of the electronic device 201 or the motion of the user carrying the electronic device 201. The gyro sensor may sense the rotation direction or rotation angle of the electronic device 201 due to movement of the user carrying the electronic device 201. The barometer may sense air pressure, and the geomagnetic sensor may sense the direction of the geomagnetism. According to an embodiment, the state of the user's motion (or movement) may be identified by the acceleration sensing information, the gyro sensing information, the air pressure sensing information, and/or the geomagnetic sensing information sensed by the motion sensor 214. For example, the user's motion state may be identified as a motionless state (e.g., stationary), a state in which no or little motion is detected (e.g., sedentary), or a moving state (or a designated user activity state (e.g., walking state or running state)).

According to an embodiment, the processor 220 may be operatively and/or electrically connected with the PPG sensor 212, the motion sensor 214, the memory 230, the display 260, the communication module 290, and/or the battery 289. The processor 220 may include a microprocessor or any suitable type of processing circuitry, such as one or more general-purpose processors (e.g., ARM-based processors), a Digital Signal Processor (DSP), a Programmable Logic Device (PLD), an Application-Specific Integrated Circuit (ASIC), a Field-Programmable Gate Array (FPGA), a Graphical Processing Unit (GPU), a video card controller, etc. In addition, it would be recognized that when a general purpose computer accesses code for implementing the processing shown herein, the execution of the code transforms the general purpose computer into a special purpose computer for executing the processing shown herein. Certain of the functions and steps provided in the Figures may be implemented in hardware, software or a combination of both and may be performed in whole or in part within the programmed instructions of a computer. No claim element herein is to be construed as means-plus-function, unless the element is expressly recited using the phrase "means for." In addition, an artisan understands and appreciates that a "processor" or "microprocessor" may be hardware in the claimed disclosure.

According to an embodiment, the processor 220 may identify a state in which there is a tremor by analyzing (or processing) the PPG signal obtained using the PPG sensor 212 and the acceleration signal obtained using the motion sensor 214. For example, the tremor may have a pattern in which signals in a predetermined frequency band is regularly repeated, which can be determined as regular vibrational involuntary motion. A tremorous state may be identified based on whether a signal pattern (trembling pattern) in a predetermined frequency band occurs (or exists) in the PPG signal and/or acceleration signal based on the monitoring the PPG signal obtained using the PPG sensor 212 and the acceleration signal obtained using the motion sensor 214.

For example, the tremor may be a regular tremor with a frequency of about 3-8 Hz, and it may be one of a resting tremor, postural tremor, or kinetic tremor. The resting tremor may be a tremor (or shake) that occurs when the user's body is in a stable state and may refer to instances where the signal pattern of a first frequency band (e.g., about 3 to 6 Hz) continuously occurs when the user is resting still. For example, resting tremor may be a typical symptom of Parkinson's disease. The postural tremor may be a tremor that occurs when the user maintains a position against gravity and may refer to instances where the signal pattern of a second frequency band (e.g., about 8 to 14 Hz) continuously occurs. The kinetic tremor may be a tremor that occurs during the user's voluntary activity (or movement) state (e.g., finger tapping, motion caused upon approaching some target (finger-to-nose-to-finger test), or a designated task, such as note taking or circle drawing) and may refer to instances where the signal pattern of a third frequency band (e.g., about 6-8 Hz) continuously occurs.

According to an embodiment, the processor 220 may analyze (or process) the first light signal (e.g., IR light signal) and second light signal (e.g., green light signal) detected (or measured) by the PPG sensor 212 and three-axis (x axis, y axis, and z axis) acceleration signals detected (or measured) by the motion sensor 214, thereby identifying a tremorous state (e.g., resting tremor, postural tremor, or kinetic tremor). According to an embodiment, the processor 220 may identify whether the signal-to-noise ratio (SNR) value of the IR light signal measured by the PPG sensor 212 is less than a designated value (e.g., a negative number). According to an embodiment, the processor 220 may monitor the respective frequencies (e.g., heart rate frequency) of the IR light signal and the green light signal. For example, the IR light signal and the green light signal each may include a first maximum peak frequency and may include a second maximum peak frequency which is a harmonic of the first maximum peak frequency. For example, the second maximum peak frequency may be twice the first maximum peak frequency, and the amplitude of the second maximum peak frequency may be smaller than the amplitude of the first maximum peak frequency. According to an embodiment, the processor 220 may identify the first maximum peak frequency and/or the second maximum peak frequency of the IR light signal. According to an embodiment, the processor 220 may identify the first maximum peak frequency and/or the second maximum peak frequency of the green light signal. According to an embodiment, the processor 220 may identify whether the first maximum peak frequency of the IR light signal and the first maximum peak frequency of the green light signal are the same (or different) . According to an embodiment, the processor 220 may identify whether the second maximum peak frequency of the IR light signal and the second maximum peak frequency of the green light signal are the same (or different). According to an embodiment, the processor 220 may identify whether the first maximum peak frequency of the IR light signal is identical to the first maximum peak frequency of the green light signal, and the second maximum peak frequency of the IR light signal is identical to the second maximum peak frequency of the green light signal.

Further, the processor 220 may identify whether there are identical frequencies among the maximum peak frequencies respectively corresponding to the three-axis (x axis, y axis, and z axis) acceleration signals measured by the motion sensor 214 and, if there are identical frequencies, identify whether the identified identical frequencies (or frequency values) are a designated frequency (e.g., 3 Hz) or more.

According to an embodiment, if the SNR value of the measured IR light signal is less than a designated value (e.g., a negative number), if there are identical frequencies among the maximum peak frequencies respectively corresponding to the three-axis (x axis, y axis, and z axis) acceleration signals, if the identical frequencies are a designated frequency (e.g., 3 Hz) or more, and if a designated (or preset) activity state is not detected, the processor 220 may identify a tremorous state. According to an embodiment, if the SNR value of the measured IR light signal is not less than a designated value (e.g., a negative number), if the first maximum peak frequency and second maximum peak frequency of the IR light signal and the first maximum peak frequency and second maximum peak frequency of the green light signal are not the same, if there are identical frequencies among the maximum peak frequencies respectively corresponding to the three-axis (x axis, y axis, and z axis) acceleration signals, if the identical frequencies are the designated frequency (e.g., 3 Hz) or more, and if the designated (or preset) activity state is not detected, the processor 220 may identify a tremorous state.

According to an embodiment, the designated activity state may include a motion state having a repetitive pattern in a predetermined period. The motion state having the repetitive pattern with the predetermined period may include a motion state in which a body part (e.g., other than the arms or hands) is shaken in the predetermined period. For example, the motion state in which the body part is shaken in the predetermined period may include a running state, a cycling state, an elliptical state, a rowing state, and a dancing state and may further include other types of motion states in which the body part is shaken in the predetermined period. According to an embodiment, if no tremorous state is identified, the processor 220 may identify a tremorless state or a designated-activity state.

According to an embodiment, in the tremorous state, the processor 220 may identify the severity of the tremor. For example, the processor 220 may identify the severity (e.g., mild, moderate, or critical) of the tremor based on the respective maximum peak frequencies of the IR light signal and the green light signal, whether there are identical frequencies among the maximum peak frequencies respectively corresponding to the three-axis (x axis, y axis, and z axis) acceleration signals, and the number of the identical frequencies. For example, the processor 220 may identify the severity of the tremor based on a numerical value. For example, if the severity may have a value between 0 and 4, the processor 220 may identify that if the severity meets $0<\text{severity}\leq 1$, it is mild, if the severity value meets $1<\text{severity}\leq 2.5$, it is moderate, and if the severity value meets $2.5<\text{severity}\leq 4$, it is critical. For example, 'mild' may refer to the case where a weak tremor occurs in a designated finger, 'moderate' may refer to the case where a weak tremor occurs overall around the finger area, and 'critical' may refer to the case where a severe tremor occurs.

According to an embodiment, if the tremorous state is identified, the processor 220 may provide information indicating the tremorous state or the severity of the tremor to the user (e.g., display it on the display 260) or may further provide additional information (e.g., information for testing the tremor or information recommending treatment or hospital information) associated with the tremorous state. According to an embodiment, if the tremorous state is identified, the processor 220 may gather data associated with the tremor and transmit the gathered data to another entity (e.g., a device of a doctor or hospital) through the communication module 290.

According to an embodiment of the present invention, the processor 220, which may include hardware module or software module (e.g., application program), may be implemented using a hardware component or software component including at least one of various sensors, input/output interface, a module for managing the state or environment of the electronic device 201, or communication module as included in the electronic device 201. According to an embodiment, the processor 220 may include, e.g., a hardware module, a software module, a firmware module, or a combination of two or more thereof. The processor 220 may omit at least some of the components or may add other components for performing the tremorous state than the above-described components. According to an embodiment, the processor 220 may be composed of at least one processor, and the at least one processor may include a main process for high-performance processing and an auxiliary processor for low-power processing, which are physically separated from each other, and it may be driven as each of the main processor and the auxiliary processor. For example, the auxiliary processor may be connected to various biometric signal measurement sensors to perform real-time (or 24-hour) monitoring on biometric signals. According to another embodiment, one processor 220 may operate. Further, one processor may operate at high performance or perform low-power processing depending on the context.

According to an embodiment, the memory 230 may store information and/or data associated with the operation of the electronic device 201. According to an embodiment, the memory 230 may store instructions that, when executed, enable the processor 220 to perform the above-described operations. For example, the memory 230 may store an application (or program) related to a function of identifying a tremorous state, a tremorless state, and/or a designated-activity state. For example, the memory 230 may store an application (or program) related to the function of identifying the severity of the tremor in the tremorous state. According to an embodiment, the memory 230 may store data used to identify the tremorous state, tremorless state, and/or designated-activity state and/or data used to identify the severity of the tremor. According to an embodiment, the memory 230 may store various data generated during execution of the program 140, as well as a program (e.g., the program 140 of FIG. 1) used for functional operation. The memory 230 may include a program area 140 and a data area (not shown). The program area may store relevant program information for driving the electronic device 201, such as an operating system (OS) (e.g., the OS 142 of FIG. 1) for booting the electronic device 201. The data area (not shown) may store transmitted and/or received data and/or generated data according to an embodiment. The memory 230 may include at least one storage medium of a flash memory, a hard disk, a multimedia card, a micro-type memory (e.g., a secure digital (SD) or an extreme digital (xD) memory), a random access memory (RAM), or a read only memory (ROM).

The display 260 according to an embodiment may display various types of information based on the control of the processor 220. For example, the display 260 may display information indicating the tremorous state and/or additional information associated with the tremorous state (e.g., information for testing the tremor or information for recommending treatment or hospital information) based on the control of the processor 220. According to an embodiment, the display 260 may be implemented as a touchscreen display. The display 260, when implemented together with an input module in the form of a touchscreen display, may display various information generated according to the user's touch. According to an embodiment, the display 260 may include at least one of a liquid crystal display (LCD), a thin film transistor LCD (TFT-LCD), an organic light emitting diode (OLED) display, a light emitting diode (LED) display, an active matrix organic LED (AMOLED) display, a micro LED display, a mini LED display, a flexible display, or a three-dimensional display. Some of the displays may be configured in a transparent type or light-transmissive type allowing the outside to be viewed therethrough. This may be configured in the form of a transparent display including a transparent OLED (TOLED) display. According to another embodiment, the electronic device 201 may further include another mounted display module (e.g., an extended display or a flexible display) in addition to the display 260.

According to an embodiment, the battery 289 may supply power to at least one component of the electronic device 201. According to an embodiment, the battery 289 may include, for example, a primary cell which is not rechargeable, a secondary cell which is rechargeable, or a fuel cell.

According to an embodiment, the communication module 290 may communicate with an electronic device (e.g., the electronic device 104 or server 108 of FIG. 1) of the outside (e.g., a doctor or a hospital) based on the control of the processor 220. According to an embodiment, the communication module 290 may transmit information indicating an occurrence of a tremorous state and/or data gathered in association with the tremor to the external electronic device based on the control of the processor 220. For example, the communication module 290 may perform at least one communication of cellular communication, ultra-wide band (UWB) communication, Bluetooth communication, and/or wireless fidelity (Wi-Fi) communication and may further perform communication in other communication schemes for communication with the external electronic device.

According to an embodiment, the electronic device 201 is not limited to the configuration illustrated in FIG. 2 and may further include various components.

According to an embodiment, the electronic device 201 may further include at least one biometric sensor associated with biometric sensing, in addition to the PPG sensor 212. For example, the at least one biometric sensor (not shown) may include a body temperature sensor, an electrocardiogram (ECG) sensor, an electrodermal activity (EDA) sensor, or/and a SWEAT sensor. According to an embodiment, the body temperature sensor may measure the body temperature. According to an embodiment, the ECG sensor may measure the electrocardiogram by sensing an electrical signal from the heart through electrodes attached to the body. According to an embodiment, the EDA sensor may include, e.g., a galvanic skin response (GSR) sensor and may sense the skin electrical activity to measure the user's arousal state. According to an embodiment, the SWEAT sensor may measure the degree of hydration and/or dehydration by sensing the sweat of the user's body. According to an embodiment, the at least one biometric sensor may provide the processor 220 with the biometric signal measured by sensing the user's biometric signal based on the control of the processor 220 or biometric signal-based information (value or numerical value) (e.g., skin temperature, electrocardiogram, stress, skin conductivity, degree of hydration, and/or degree of dehydration) measured by sensing the user's biometric signal.

According to an embodiment, the electronic device 201 may further include an audio module (not shown) (e.g., the audio module 170 of FIG. 1) or a vibration module (not shown) (e.g., the haptic module 179 of FIG. 1). The audio module may output sounds and may include at least one of, e.g., an audio codec, a microphone (MIC), a receiver, an earphone output (EAR_L) or a speaker. The audio module may output, as an audio signal, information indicating the tremorous state and/or additional information associated with the tremorous state (e.g., information for testing the tremor or information for recommending treatment or hospital information) based on the control of the processor 220. For example, the vibration module may output a vibration associated with information indicating the tremorous state and/or additional information associated with the tremorous state (e.g., information for testing the tremor or information for recommending treatment or hospital information) based on the control of the processor 220.

According to an embodiment, the electronic device 201 may further include a GNSS module. The GNSS module may measure the position of the electronic device 201 or the user based on a signal from a satellite. For example, the GNSS module may be a global navigation satellite system (GLONASS) or a European satellite navigation system (GALILEO). The electronic device 201 may include another system (e.g., GPS aided geo augmented navigation (GAGAN)) similar to the GNSS module and capable of satellite-based positioning.

In the above-described embodiment, major components of the electronic device 201 have been described above in connection with FIG. 2. According to an embodiment, however, not all of the components of FIG. 2 are not essential components, and the electronic device 201 may be implemented with more or less components than those shown.

According to an embodiment, an electronic device (e.g., the electronic device 101 of FIG. 1 or the electronic device 201 of FIG. 2) may comprise a communication module (e.g., the communication module 190 of FIG. 1 or the communication module 290 of FIG. 2), a display (e.g., the display 160 of FIG. 1 or the display 260 of FIG. 2), a PPG sensor (e.g., the sensor module 176 of FIG. 1 or the PPG sensor 212 of FIG. 2), a motion sensor (e.g., the sensor module 176 of FIG. 1 or the motion sensor 214 of FIG. 2), a memory (e.g., the memory 130 of FIG. 1 or the memory 230 of FIG. 2), and at least one processor (e.g., the processor 120 of FIG. 1 or the processor 220 of FIG. 2). The at least one processor may be configured to obtain a first light signal and a second light signal sensed by the PPG sensor and three-axis acceleration signals sensed by the motion sensor, identify a tremorous state using the first light signal, the second light signal, and the three-axis acceleration signals, and display information indicating the tremorous state on the display.

According to an embodiment, the at least one processor further may be configured to identify a severity of the tremorous state upon identifying the tremorous state.

According to an embodiment, the at least one processor further may be configured to transmit the information indicating the tremorous state through the communication module to an external electronic device.

According to an embodiment, the first light signal may include an infrared (IR) light signal, and the second light signal includes a green light signal.

According to an embodiment, the at least one processor further may be configured to identify the tremorous state if an SNR value of the IR light signal is less than a designated value, there are identical frequencies in maximum peak frequencies of the three-axis acceleration signals, the identical frequencies are a designated frequency or more, and a user's activity state is not a designated-activity state.

According to an embodiment, the at least one processor further may be configured to identify the tremorous state if a signal-to-noise ratio (SNR) value of the IR light signal is greater than a designated value, a first maximum peak frequency and a second maximum peak frequency of the IR light signal are different from a first maximum peak frequency and a second maximum peak frequency of the green light signal, there are identical frequencies in maximum peak frequencies of the three-axis acceleration signals, the identical frequencies are a designated frequency or more, and a user's activity state is not a designated-activity state.

According to an embodiment, the designated frequency may be 3 Hz.

According to an embodiment, the at least one processor may be configured to identify a tremorless state based on the SNR value of the IR light signal being greater than the designated value, and a first maximum peak frequency and a second maximum peak frequency of the IR light signal being identical to a first maximum peak frequency and a second maximum peak frequency of the green light signal.

According to an embodiment, the at least one processor further may be configured to identify a voluntarily active state if the identical frequencies are absent, or if the identical frequencies are less than the designated frequency, or if the user's activity state is the designated-activity state.

According to an embodiment, the at least one processor further may be configured to control the display to display a screen for a tremor test based on identifying the tremorous state.

According to an embodiment, the at least one processor further may be configured to display a hospital associated service screen on the display based on identifying the tremorous state.

Figure 3:
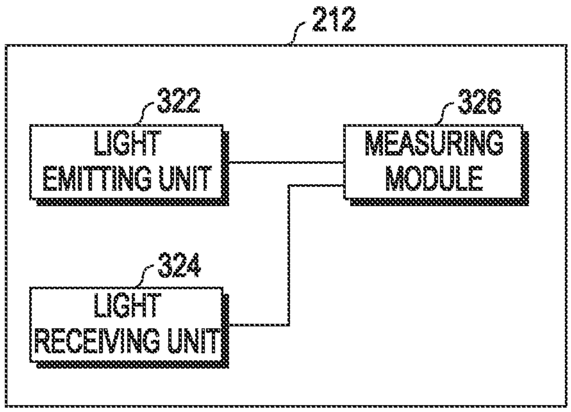
FIG. 3 is a block diagram of a PPG sensor according to an embodiment.

FIG. 3 is a block diagram of a PPG sensor according to an embodiment.

Referring to FIG. 3, according to an embodiment, the PPG sensor 212 may include a light emitting unit 322, a light receiving unit 324, and a measuring module 326.

According to an embodiment, the light emitting unit 322 may include at least one of a spectrometer, a vertical cavity surface emitting laser (VCSEL), an LED, a white LED, and a white laser. For example, the light emitting unit 322 may output IR light and/or visible light (red light, green light, or blue light) through a spectrometer, VCSEL, LED, white LED, or white laser.

According to an embodiment, the light receiving unit 324 may include at least one light receiving element. For example, the light receiving element may include at least one of an avalanche photodiode (PD), a single photon avalanche diode (SPAD), a photodiode, a photomultiplier tube (PMT), a charge-coupled device (CCD), a complementary metal-oxide-semiconductor (CMOS) array, or a spectrometer. For example, the structure of the light receiving unit 324 may be of a reflective type or a transmissive type. According to an embodiment, the at least one light receiving element may receive (detect or sense) the light emitted by the light emitting unit 322 and reflected by the wearer's body (e.g., skin, skin tissue, fat layer, vein, artery or capillary). For example, the light receiving unit 324 may output an electrical signal corresponding to the light sensed by the at least one light receiving element. According to an embodiment, the at least one light receiving element may sense a first wavelength of first light (e.g., IR light) and a second wavelength of second light (e.g., green light) partially absorbed by the body and partially reflected after the body of the IR light and green light output by the light emitting unit 322 are radiated to the body (e.g., skin). For example, the first wavelength of first light may differ from the second wavelength of second light in their penetration depth based on the physical constitutional characteristics. For example, the first wavelength of first light may be light sensitive to dynamic noise (or motion) due to the penetration depth based on the physical constitutional characteristics as compared with the second wavelength of second light. For example, the sensed light signal may include a noise component due to the motion when the light sensing operation is performed and, if light detection is performed during the motion, the IR light signal may include more motion-induced noise components than the green light signal.

According to an embodiment, the measuring module 326 (processing unit or IC) may be electrically connected with the light emitting unit 322, the light receiving unit 324, and the processor 220. According to an embodiment, the measuring module 326 may measure blood pressure, blood sugar, heart rate, and/or blood volume based on electrical signals corresponding to the light sensed by the light receiving unit 324 (e.g., the amount of reflected light). According to an embodiment, the measuring module 326 is implemented as blood pressure, blood sugar, heart rate, and/or blood volume measurement algorithms so that the processor 220 may perform operations according to the blood pressure, blood sugar, heart rate, and/or blood volume measurement algorithm. According to an embodiment, the measuring module 326 may obtain an IR light signal based on an electrical signal corresponding to the IR light (e.g., the amount of reflected IR light) sensed by the light receiving unit 324 and may obtain a green light signal based on an electrical signal corresponding to the green light (e.g., the amount of reflected green light) sensed by the light receiving unit 324. According to an embodiment, the measuring module 326 may transfer the IR light signal and the green light signal to the processor 220 or may process it on its own.

According to an embodiment, the components included in the PPG sensor 212 may not be limited to the light emitting unit 322, the light receiving unit 324, and/or the measuring module 326. For example, the PPG sensor 212 may further include a signal processing unit (not shown) (e.g., an analog front end). The signal processing unit (not shown) may include an amplifier for amplifying biometric signals and an analog to digital converter (ADC) for converting analog biometric signals into digital biometric signals. However, the components included in the signal processing unit may not be limited to the above-described amplifier and ADC. According to certain embodiments, the electronic device 201 may include a plurality of light emitting units 322 and/or a plurality of light receiving units 324, and the light emitting units 322 and the light receiving units 324 may configure at least one array. According to certain embodiments, different weights may be applied to the light emitting units 322 and/or light receiving units 324 (or biometric signals obtained from the plurality of light emitting units 322 and/or light receiving units 324). According to certain embodiments, the PPG sensor 212 may be disposed on the housing of the electronic device 201 or may be disposed to be visually exposed through the housing. The placement position or direction of the PPG sensor 212 is described in more detail with reference to the drawings to be described below.

Figure 4:
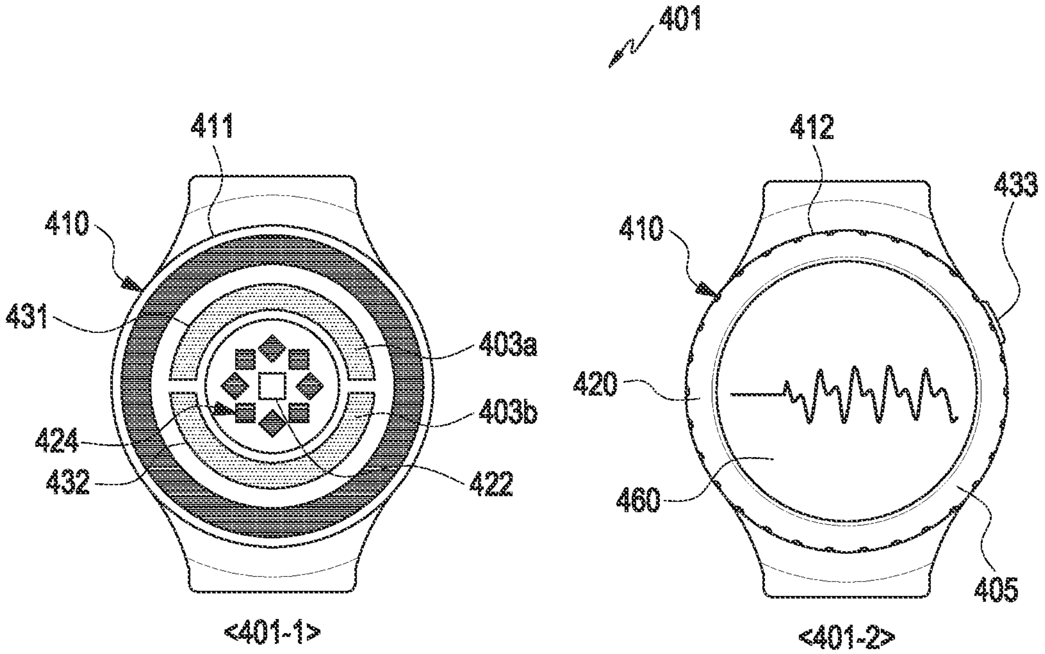
FIG. 4 is a view illustrating an example in which an electronic device is implemented as a wearable electronic device according to an embodiment.

FIG. 4 is a view illustrating an example in which an electronic device is implemented as a wearable electronic device according to an embodiment.

Referring to FIG. 4, according to an embodiment, the electronic device 201 may be implemented as a wearable electronic device 401 to obtain biometric information by performing sensing operations on the user's body. According to another embodiment, the electronic device 201 may also receive biometric information sensed by another wearable device through communication with the other wearable electronic device. According to an embodiment, the wearable electronic device 401 may be, e.g., a wearable device in the form of a wrist watch, which may be worn on the user's wrist or the wearable device that may be worn on another portion of the body (e.g., head, forearm, thigh, or another body portion where heart rate may be measured). The electronic device 401 according to an embodiment may include a housing 410 including a first surface 411 (e.g., rear surface), a second surface 412 (e.g., front surface), and a third surface (e.g., side surface) surrounding a space between the first surface 411 (e.g., rear surface) and second surface 412 (e.g., rear surface).

Referring to <401-1> of FIG. 4, the light emitting unit 422 (e.g., the light emitting unit 322 of FIG. 3) and the light receiving unit 424 (e.g., the light receiving unit 324 of FIG. 3) which are parts of the PPG sensor may be disposed on the first surface 411 (e.g., rear surface) of the housing 410. The light emitting unit 422 and the light receiving unit 424 may be disposed on the first surface 411 (e.g., rear surface) of the electronic device 201 to be able to contact the user's body portion (e.g., wrist) when the electronic device 401 is worn. The first electrode 431 and the second electrode 432, which are parts of the ECG sensor, may be disposed on at least two portions of the first member 403*a* and 403*b* disposed to surround the light emitting unit 422 and the light receiving unit 424.

Referring to <401-2> of FIG. 4, according to an embodiment, in the electronic device 401, the display 460 (e.g., the display 260 of FIG. 2) may be disposed on the second surface 412 (e.g., front surface), which is another surface of the housing 410. According to an embodiment, the third electrode 433, which is another portion of the ECG sensor, may be disposed on at least one portion of the second member 405 formed in a shape surrounding the display 460. According to an embodiment, when the electronic device 401 is worn, the third electrode 433 may be disposed on at least one portion of the housing 410 so as not to come into contact with the user's body portion. According to an embodiment, the third electrode 433 may be disposed on the second surface 412 (e.g., the front surface) of the electronic device 401. For example, the third electrode 433 may be disposed on or included in the display 460 in the form of a transparent electrode (e.g., indium tin oxide, ITO).

According to an embodiment, as the light radiated to the body by the light emitting unit 422 is reflected by the user's body part (e.g., wrist) and is sensed by the light receiving unit 424, the PPG sensor may sense the IR light signal and/or the green light signal.

According to an embodiment, the PPG sensor 212 (e.g., the light emitting unit 422 and the light receiving unit 424) may be activated and start its operation (e.g., sensing operation) when the electronic device 401 is powered on or during a designated event (e.g., an event by application execution or a user input). Further, it is possible to further sense the user's additional biometric signal using the first electrode 431, the second electrode 432, the third electrode 433, and another biometric sensor (not shown) (e.g., temperature sensor, ECG sensor, EDA sensor, and/or SWEAT sensor).

The user's electrocardiogram, stress, skin conductivity, and/or skin temperature may be measured based on the measured biometric signal.

Figure 5:
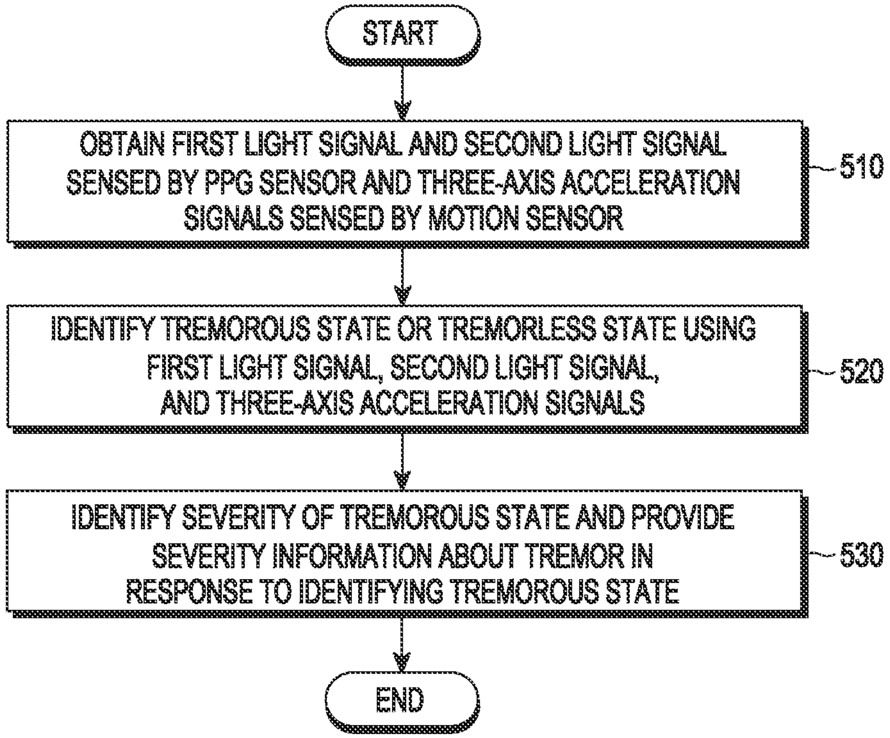
FIG. 5 is a flowchart illustrating a tremor detection operation in an electronic device according to an embodiment.

FIG. 5 is a flowchart illustrating a tremor detection operation in an electronic device according to an embodiment.

Referring to FIG. 5, according to an embodiment, a processor (e.g., the processor 120 of FIG. 1 or the processor 220 of FIG. 2) of an electronic device (e.g., the electronic device 101 of FIG. 1, the electronic device 201 of FIG. 2, or the electronic device 401 of FIG. 4) may perform at least one of operations 510 to 530.

In operation 510, according to an embodiment, the processor 220 may obtain a first light signal (e.g., IR light signal) and a second light signal (e.g., green light signal) sensed by the PPG sensor 212 and three-axis (x axis, y axis, and z axis) acceleration signals sensed by the motion sensor.

In operation 520, according to an embodiment, the processor 220 may detect (or identify) a tremorous state (e.g., THE state of resting tremor, postural tremor, or kinetic tremor) or a tremorless state (or designated-activity state) using the first light signal (e.g., IR light signal), the second light signal (e.g., green light signal), and three-axis acceleration signals.

According to an embodiment, the processor 220 may identify whether the signal-to-noise ratio (SNR) value of the IR light signal is less than a designated value (e.g., a negative number). According to an embodiment, the processor 220 may monitor the frequencies (e.g., heart rate frequency) of the IR light signal and the green light signal. For example, the IR light signal and the green light signal each may include a first maximum peak frequency and a second maximum peak frequency which is a harmonic of the first maximum peak frequency. For example, the second maximum peak frequency may be twice the first maximum peak frequency, and the amplitude of the second maximum peak frequency may be smaller than the amplitude of the first maximum peak frequency. According to an embodiment, the processor 220 may identify whether the first maximum peak frequency and second maximum peak frequency of the IR light signal are identical to (or different from) the first maximum peak frequency and second maximum peak frequency of the green light signal. For example, when the first maximum peak frequency and second maximum peak frequency of the IR light signal are identical to the first maximum peak frequency and second maximum peak frequency of the green light signal, that may mean that the frequency component due to heart rate is identically in both the IR light signal and green light signal, so that the noise caused by tremors or movements other than the heart rate is insignificant or absent.

According to an embodiment, the processor 220 may identify whether there are identical frequencies in the maximum peak frequencies of the three-axis (x axis, y axis, and z axis) acceleration signals and, if there are identical frequencies, identify whether the identical frequencies are a designated frequency (e.g., 3 Hz) or more. For example, assuming that the heartbeat frequency is 60 or 80 beats per minute in the motionless state, each of the three-axis acceleration signals may be about 1 to 2 Hz, i.e., less than 3 Hz, and if the three-axis acceleration signals have 3 Hz or more signals, it may mean that the user is in a moving state or a motion state (e.g., the designated-activity state).

According to an embodiment, if the SNR value of the IR light signal is less than a designated value (e.g., a negative number), if there are identical frequencies in the maximum peak frequencies of to the three-axis acceleration signals, if the identical frequencies are a designated frequency (e.g., 3 Hz) or more, and if the user's activity state is not the designated-activity state, the processor 220 may detect a tremorous state. According to an embodiment, if the SNR value of the IR light signal is not less than a designated value (e.g., a negative number), if the first maximum peak frequency and second maximum peak frequency of the IR light signal and the first maximum peak frequency and second maximum peak frequency of the green light signal are not the same, if there are identical frequencies in the maximum peak frequencies of the three-axis (x axis, y axis, and z axis) acceleration signals, if the identical frequencies are the designated frequency (e.g., 3 Hz) or more, and the designated (or preset) activity state is not detected, the processor 220 may identify a tremorous state. According to an embodiment, the designated activity state may include a motion state having a repetitive pattern in a predetermined period. The motion state having a repetitive pattern with a predetermined period may include a motion state in which a body part (e.g., the body than the arms or hands) is shaken in the predetermined period. For example, the motion state in which the body part is shaken in the predetermined period may include a running state, a cycling state, an elliptical state, a rowing state, and a dancing state and may further include other types of motion states in which the body part is shaken in the predetermined period.

According to an embodiment, if no tremorous state is detected, the processor 220 may identify a tremorless state (or user acting state).

In operation 530, according to an embodiment, the processor 220 may identify the severity of the tremor and provide severity information about the tremor in response to detection of the tremorous state.

Figure 6:
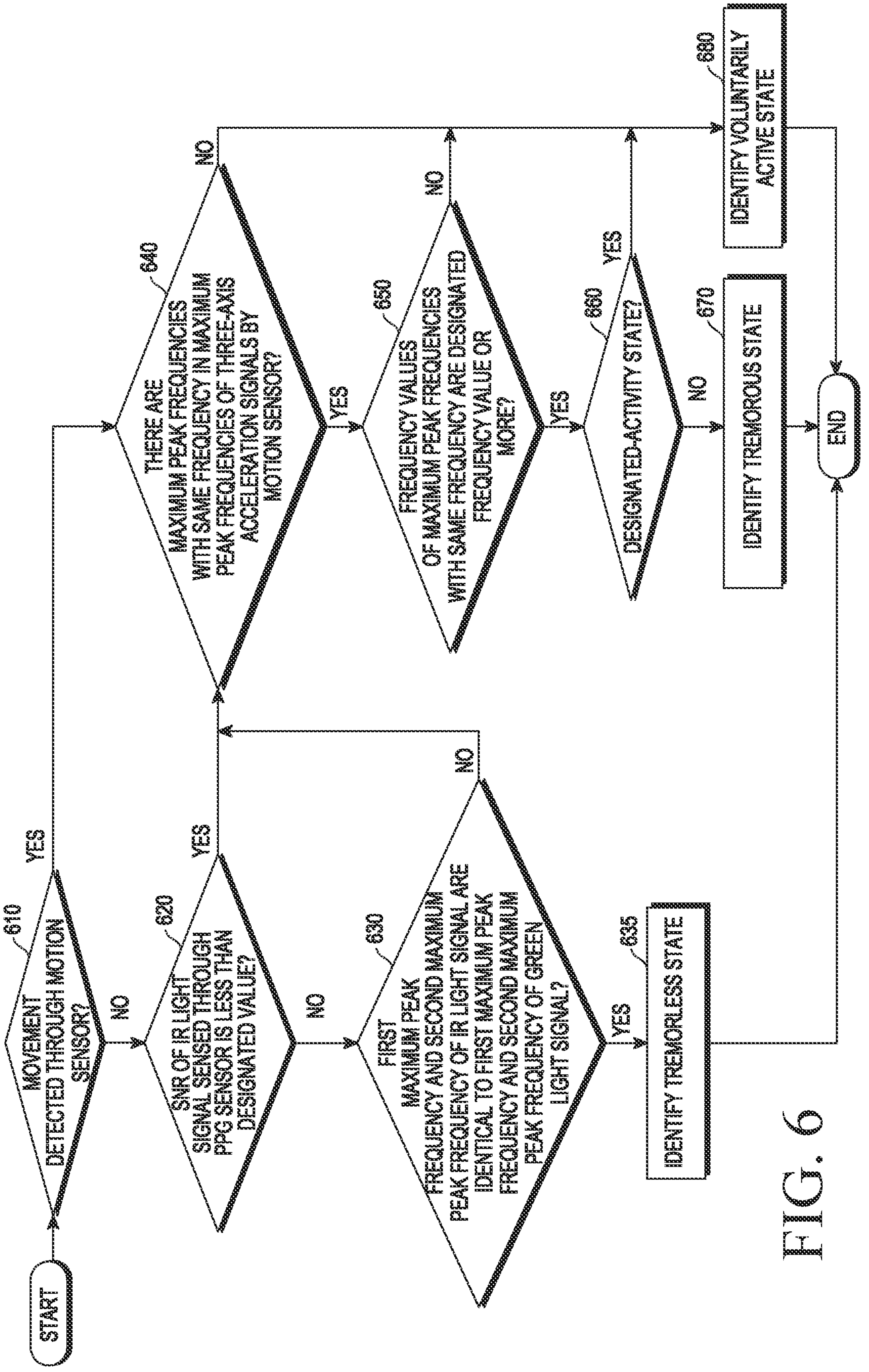
FIG. 6 is a flowchart illustrating an operation of detecting a tremorless state, a tremorous state, and a voluntary user activity state in an electronic device according to an embodiment.

FIG. 6 is a flowchart illustrating an operation of detecting a tremorless state, a tremorous state, and a voluntary user activity state in an electronic device according to an embodiment.

Referring to FIG. 6, according to an embodiment, a processor (e.g., the processor 120 of FIG. 1 or the processor 220 of FIG. 2) of an electronic device (e.g., the electronic device 101 of FIG. 1, the electronic device 201 of FIG. 2, or the electronic device 401 of FIG. 4) may perform at least one of operations 610 to 680.

In operation 610, according to an embodiment, the processor 220 may identify whether a movement of the electronic device 201 is detected through the motion sensor 214 based on an occurrence of a designated event (tremor detection start event) or a user request (tremor detection request). For example, the consumption current of the PPG sensor 212 may be larger than the consumption current of the motion sensor 214, and the PPG sensor 212 may be more sensitive to tiny tremors than the motion sensor 214. Accordingly, the processor 220 may use the motion sensor 214, first, to identify whether a movement is detected so that if a movement is detected through the motion sensor 214, tremor detection may be performed using the motion sensor 214. If no movement is detected through the motion sensor 214, the PPG sensor 212, which is more motion sensitive than the motion sensor 214, may be turned on (or activated or driven) so that the PPG sensor 212 and the motion sensor 214 both may be used to perform tremor detection.

In operation 620, according to an embodiment, if no movement is detected through the motion sensor 214, the processor 220 may identify whether the SNR of the first light signal (IR light signal) sensed using the PPG sensor 212 is less than a designated value. According to an embodiment, if no movement is detected through the motion sensor 214, the processor 220 may turn on (or activate or drive) the PPG sensor 212, which is more motion sensitive than the motion sensor 214, to obtain an IR light signal. The processor 220 may obtain the SNR (SNR=10 log 10(S/N)) based on the actual IR light signal magnitude (S) and noise magnitude (N) included in the IR light signal sensed using the PPG sensor 212 and identify whether the SNR value is less than 0 (e.g., a negative number). When the SNR value is greater than 0, it may mean that the magnitude of the IR light signal is larger than the magnitude of noise (due to tremor). If the magnitude of the IR light signal is larger than the noise magnitude, the tremor-induced noise may be disregarded.

In operation 630, according to an embodiment, the processor 220 may further obtain the second light signal (green light signal) using the PPG sensor 212 based on the SNR of the IR light signal being not less than the designated value and identify whether the first maximum peak frequency and second maximum peak frequency of the IR light signal are identical to the first maximum peak frequency and second maximum peak frequency of the green light signal. For example, the processor 220 may convert the IR light signal and green light signal in the time domain into the IR light signal and green light signal in the frequency domain and compare the frequency of the IR light signal with the frequency of the green light signal. For example, the IR light signal and green light signal of the frequency domain may include the first maximum peak frequency (1st maximum peak frequency) corresponding to the heartbeat frequency and the second maximum peak frequency (2nd maximum peak frequency) corresponding to the first harmonic frequency (1st harmonic frequency=2*1st maximum peak frequency) in the harmonic frequencies of the heartbeat frequency and may further include other peak frequencies. For example, the processor 220 may identify whether the first maximum peak frequency of the IR light signal is identical to the first maximum peak frequency of the green light signal, and the second maximum peak frequency of the IR light signal is identical to the second maximum peak frequency of the green light signal. When the first maximum peak frequency of the IR light signal is identical to the first maximum peak frequency of the green light signal and the second maximum peak frequency of the IR light signal is identical to the second maximum peak frequency of the green light signal, it may mean that there is no difference in noise between the IR light signal and the green light signal, and that there is no difference in noise may mean that the IR light signal and the green light signal each has no or little noise due to movement (e.g., tremor).

In operation 635, according to an embodiment, the processor 220 may identify a tremorless state based on the SNR value of the IR light signal being not less than the designated value (e.g., a negative number) and the first maximum peak frequency and second maximum peak frequency of the IR light signal being identical to the first maximum peak frequency and second maximum peak frequency of the green light signal.

In operation 640, according to an embodiment, if a movement is detected through the motion sensor, or if the SNR value of the IR light signal is less than the designated value (e.g., a negative number) when no movement is detected through the motion sensor, or the first maximum peak frequency and second maximum peak frequency of the IR light signal are not identical to the first maximum peak frequency and second maximum peak frequency of the green light signal, respectively, when no movement is detected through the motion sensor and the SNR value of the IR light signal is not less than the designated value (e.g., a negative number), the processor 220 may identify whether there are maximum peak frequencies with the same frequency in the maximum peak frequencies of the three-axis acceleration signals sensed by the motion sensor 214. For example, the processor 220 may convert the three-axis (x axis, y axis, and z axis) acceleration signals in the time domain into three-axis acceleration signals in the frequency domain and compare the respective frequencies of the three-axis acceleration signals. For example, the processor 220 may perform comparison to determine whether the first maximum peak frequency of the x-axis acceleration signal, the first maximum peak frequency of the y-axis acceleration signal, and the first maximum peak frequency of the z-axis acceleration signal are identical, perform comparison to determine whether the second maximum peak frequency of the x-axis acceleration signal, the second maximum peak frequency of the y-axis acceleration signal, and the second maximum peak frequency of the z-axis acceleration signal are identical, and identify whether there is the same first maximum peak frequency or the same second maximum peak frequency. For example, that the first maximum peak frequency and/or second maximum peak frequency of each axis is the same may mean that there is a movement that repeats at a predetermined frequency, like a tremor.

In operation 650, according to an embodiment, if there are maximum peak frequencies with the same frequency in the maximum peak frequencies of the axes, the processor 220 may identify whether the maximum peak frequencies with the same frequency are a designated frequency or more (e.g., 3 Hz or more). For example, the frequency of the acceleration signal due to the tremor may be 3 Hz or more.

In operation 660, according to an embodiment, if there are maximum peak frequencies with the same frequency in the maximum peak frequencies of the axes, and the maximum peak frequencies with the same frequency are the designated frequency or more, the processor 220 may identify whether the user is in a state of doing a designated activity. For example, the designated-activity state may be an activity state that may be mistaken for tremor and may be an activity in which there are maximum peak frequencies with the same frequency in the maximum peak frequencies of the axes, and the maximum peak frequencies with the same frequency are the designated frequency or more. According to an embodiment, the designated activity state may include a motion state having a repetitive pattern in a predetermined period. The motion state having a repetitive pattern with a predetermined period may include a motion state in which a body part (e.g., the body than the arms or hands) is shaken in the predetermined period. For example, the motion state in which the body part is shaken in the predetermined period may include a running state, a cycling state, an elliptical state, a rowing state, and a dancing state and may further include other types of motion states in which the body part is shaken in the predetermined period. For example, the designated-activity state may include an arm moving state by walking or running or a keyboard typing state. The processor 220 may identify whether the user's activity state is the designated-activity state through the motion sensor 214.

In operation 670, according to an embodiment, if there are identical frequencies in the maximum peak frequencies of the three-axis acceleration signals, and the identical frequencies are a designated frequency (e.g., 3 Hz) or more, and the user's activity state is not the designated-activity state, the processor 220 may identify a tremorous state.

In operation 680, according to an embodiment, if there are no identical frequencies in the maximum peak frequencies of the three-axis acceleration signals, or if there are identical frequencies in the maximum peak frequencies of the three-axis acceleration signals, but the identical frequencies are not the designated frequency (e.g., 3 Hz), or if the user's activity state is the designated activity state, the processor 220 may identify the voluntary active state (e.g., a tremorless, voluntarily active state).

According to an embodiment, a method for detecting a tremor in an electronic device (e.g., the electronic device 101 of FIG. 1, the electronic device 201 of FIG. 2, or the electronic device 401 of FIG. 4) may include obtaining a first light signal and a second light signal sensed by a PPG sensor of the electronic device and three-axis acceleration signals sensed by a motion sensor of the electronic device, identifying a tremorous state using the first light signal, the second light signal, and the three-axis acceleration signals, and displaying information indicating the tremorous state on the display.

According to an embodiment, the method may further comprise identifying a severity of the tremorous state upon identifying the tremorous state.

According to an embodiment, the method may further comprise transmitting the information indicating the tremorous state to an external electronic device through a communication module of the electronic device.

According to an embodiment, the first light signal may include an infrared (IR) light signal, and the second light signal includes a green light signal.

According to an embodiment, the method may further comprise identifying the tremorous state if an SNR value of the IR light signal is less than a designated value, there are identical frequencies in maximum peak frequencies of the three-axis acceleration signals, the identical frequencies are a designated frequency or more, and a user's activity state is not a designated-activity state.

According to an embodiment, the method may further comprise identifying the tremorous state if a signal-to-noise ratio (SNR) value of the IR light signal is greater than a designated value, a first maximum peak frequency and a second maximum peak frequency of the IR light signal are different from a first maximum peak frequency and a second maximum peak frequency of the green light signal, there are identical frequencies in maximum peak frequencies of the three-axis acceleration signals, the identical frequencies are a designated frequency or more, and a user's activity state is not a designated-activity state.

According to an embodiment, the method may further comprise identifying a tremorless state based on the SNR value of the IR light signal being greater than the designated value, and a first maximum peak frequency and a second maximum peak frequency of the IR light signal being identical to a first maximum peak frequency and a second maximum peak frequency of the green light signal.

According to an embodiment, the method may further comprise identifying a voluntarily active state if the identical frequencies are absent, or if the identical frequencies are less than the designated frequency, or if the user's activity state is the designated-activity state.

According to an embodiment, the method may further comprise displaying a screen for a tremor test on the display of the electronic device based on identifying the tremorous state.

According to an embodiment, the method may further comprise displaying a hospital associated service screen based on identifying the tremorous state.

Figure 7:
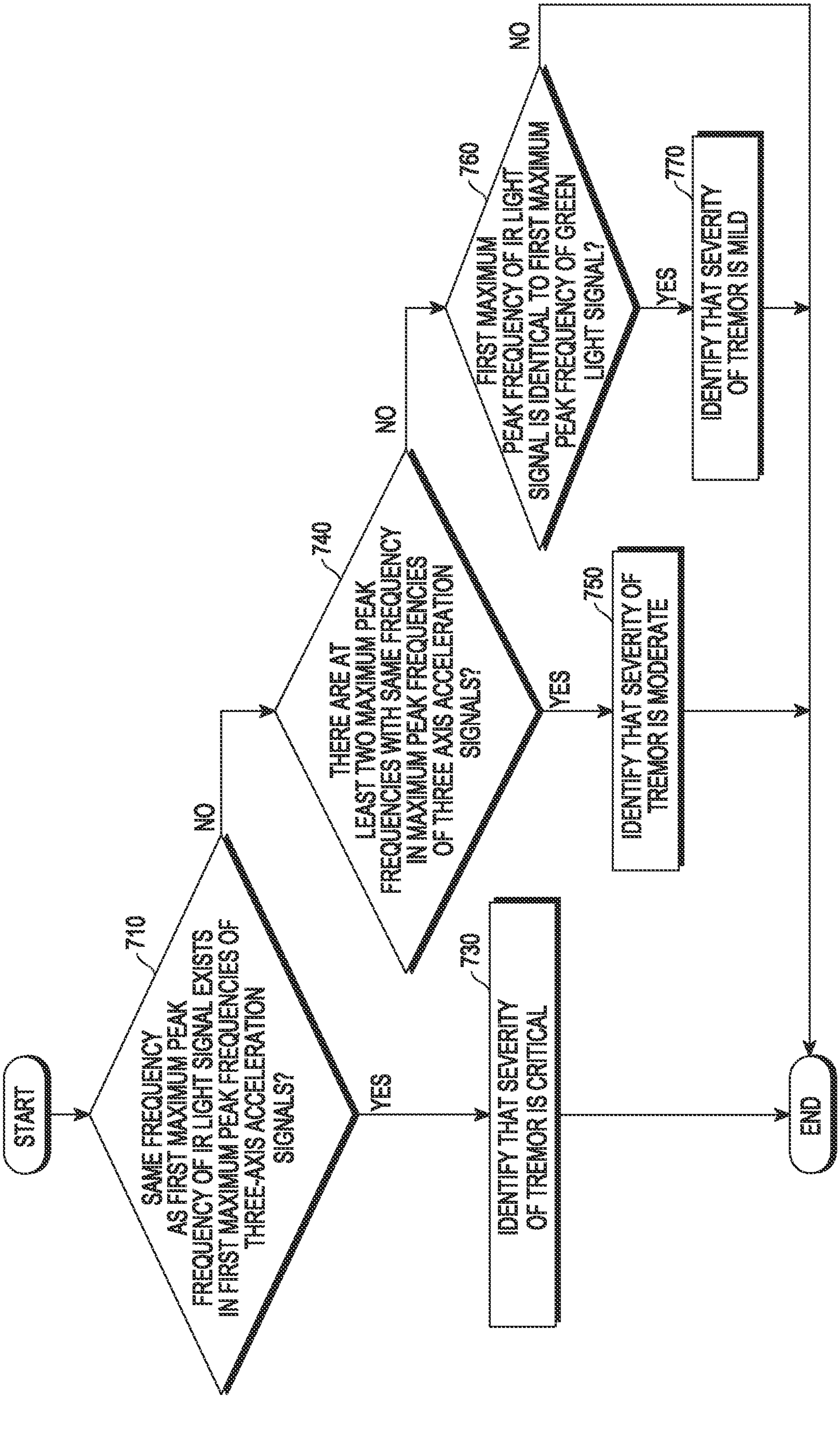
FIG. 7 is a flowchart illustrating an operation of identifying the severity of a tremor in an electronic device according to an embodiment.

FIG. 7 is a flowchart illustrating an operation of identifying the severity of a tremor in an electronic device according to an embodiment.

Referring to FIG. 7, according to an embodiment, a processor (e.g., the processor 120 of FIG. 1 or the processor 220 of FIG. 2) of an electronic device (e.g., the electronic device 101 of FIG. 1, the electronic device 201 of FIG. 2, or the electronic device 401 of FIG. 4) may perform at least one of operations 710 to 770.

In operation 710, according to an embodiment, the processor 220 may identify whether the same frequency as the first maximum peak frequency of the IR light signal sensed by the PPG sensor 212 exists in the first maximum peak frequencies of the three-axis (x axis, y axis, and z axis) acceleration signals sensed by the motion sensor 214. When a tremor occurs, the frequency component due to the tremor may appear in the IR light signal, as well as the three-axis acceleration signals. Thus, if the first maximum peak frequency of the IR light signal is identical to at least one of the first maximum peak frequencies of the three-axis acceleration signals, it may mean that tremor is occurring.

In operation 730, according to an embodiment, if the same frequency as the first maximum peak frequency of the IR light signal exists in the first maximum peak frequencies of the three-axis acceleration signals, the processor 220 may identify that the tremor severity is critical (e.g., $2.5<\text{severity}\leq 4$). According to an embodiment, the strength (e.g., severity) of the tremor may be correlated to the degree of tuning between the frequency component of the signal (e.g., IR light signal) sensed by the PPG sensor 212 and the signals (e.g., three-axis acceleration signals) sensed by the motion sensor 214. For example, as the frequency component of the signal (e.g., IR light signal) sensed by the PPG sensor 212 and the frequency component of the signals (e.g., three-axis acceleration signals) sensed by the motion sensor 214 are increasingly similar, that may indicate that the strength of the tremor is increased (the severity may be closer to 'critical'). According to an embodiment, 1) as the number of frequencies identical to the first maximum peak frequency of the IR light signal increases (the consistency between the IR light signal and the three-axis acceleration signals increases), 2) as the number of first maximum peak frequencies in the first maximum peak frequencies of the three-axis acceleration signals, that differ from the first maximum peak frequency of the IR light signal within a designated value (e.g., 0.2 Hz), increases (or as the error rate reduces), 3) if the same frequency as the second maximum peak frequency of the IR light signal exists in the second maximum peak frequencies of the three-axis acceleration signals, and as the number of frequencies identical to the second maximum peak frequency of the IR light signal increases (as the consistency rate between the IR light signal and the three-axis acceleration signals increases), or 4) as the number of second maximum peak frequencies in the second maximum peak frequencies of the three-axis acceleration signals, that differ from the second maximum peak frequency of the IR light signal within a designated value (0.2 Hz) (or as the error rate reduces), the processor 220 may determine that the severity value (e.g., the strength value of the tremor) is a value within a critical severity value range (e.g., $2.5<\text{severity}\leq 4$).

In operation 740, according to an embodiment, if the same frequency as the first maximum peak frequency of the IR light signal does not exist in the first maximum peak frequencies of the three-axis acceleration signals, the processor 220 may identify whether at least two maximum peak frequencies with the same frequency exist in the maximum peak frequencies of the three-axis acceleration signals.

In operation 750, according to an embodiment, if at least two maximum peak frequencies with the same frequency exist in the maximum peak frequencies of the three-axis acceleration signals, the processor 220 may identify that the severity of the tremor is moderate (e.g., 1<severity≤2.5). According to an embodiment, 1) as the number of identical maximum peak frequencies in the maximum peak frequencies of the three-axis acceleration signals increases (or as the consistency rate of the three-axis acceleration signals increases) or 2) if the number of maximum peak frequencies with a difference within a designated value (e.g., 0.2 Hz) between the maximum peak frequencies of the three-axis acceleration signals increases (or as the error rate reduces, the processor 220 may determine that the severity value (e.g., the strength value of the tremor) is a value within the moderate severity value range (e.g., 1<severity≤2.5).

In operation 760, according to an embodiment, if the same frequency as the first maximum peak frequency of the IR light signal does not exist in the first maximum peak frequencies of the three-axis acceleration signals, and at least two maximum peak frequencies with the same frequency do not exist in the maximum peak frequencies of the three-axis acceleration signals, the processor 220 may identify whether the first maximum peak frequency of the IR light signal is identical to the first maximum peak frequency of the green light signal.

In operation 770, according to an embodiment, if the same frequency as the first maximum peak frequency of the IR light signal does not exist in the first maximum peak frequencies of the three-axis acceleration signals, and at least two maximum peak frequencies with the same frequency do not exist in the maximum peak frequencies of the three-axis acceleration signals, and the first maximum peak frequency of the IR light signal is identical to the first maximum peak frequency of the green light signal, the processor 220 may identify that the severity of the tremor is mild (e.g., 0<severity≤1). According to an embodiment, 1) as the error rate reduces with a difference within a designated value (e.g., 0.2 Hz) between the second maximum peak frequency of the IR light signal and the second maximum peak frequency of the green light signal, 2) as the number of identical maximum peak frequencies in the maximum peak frequencies of the three-axis acceleration signals increases (or as the consistency rate of the three-axis acceleration signals increases) or 3) if the number of maximum peak frequencies with a difference within a designated value (e.g., 0.2 Hz) between the maximum peak frequencies of the three-axis acceleration signals increases (or as the error rate reduces), the processor 220 may determine that the severity value (e.g., the strength value of the tremor) is a value within the mild severity value range (e.g., 0<severity≤1).

Although in the example described in connection with FIG. 7, the overall severity value range is designated as 0<severity≤4, and within the overall severity value range, the severity is divided into a critical, moderate, and mild range and is identified, the severity range may be selectively set to be narrower or wider, and the strength of severity may also be divided into more or less strengths.

Figure 8A:
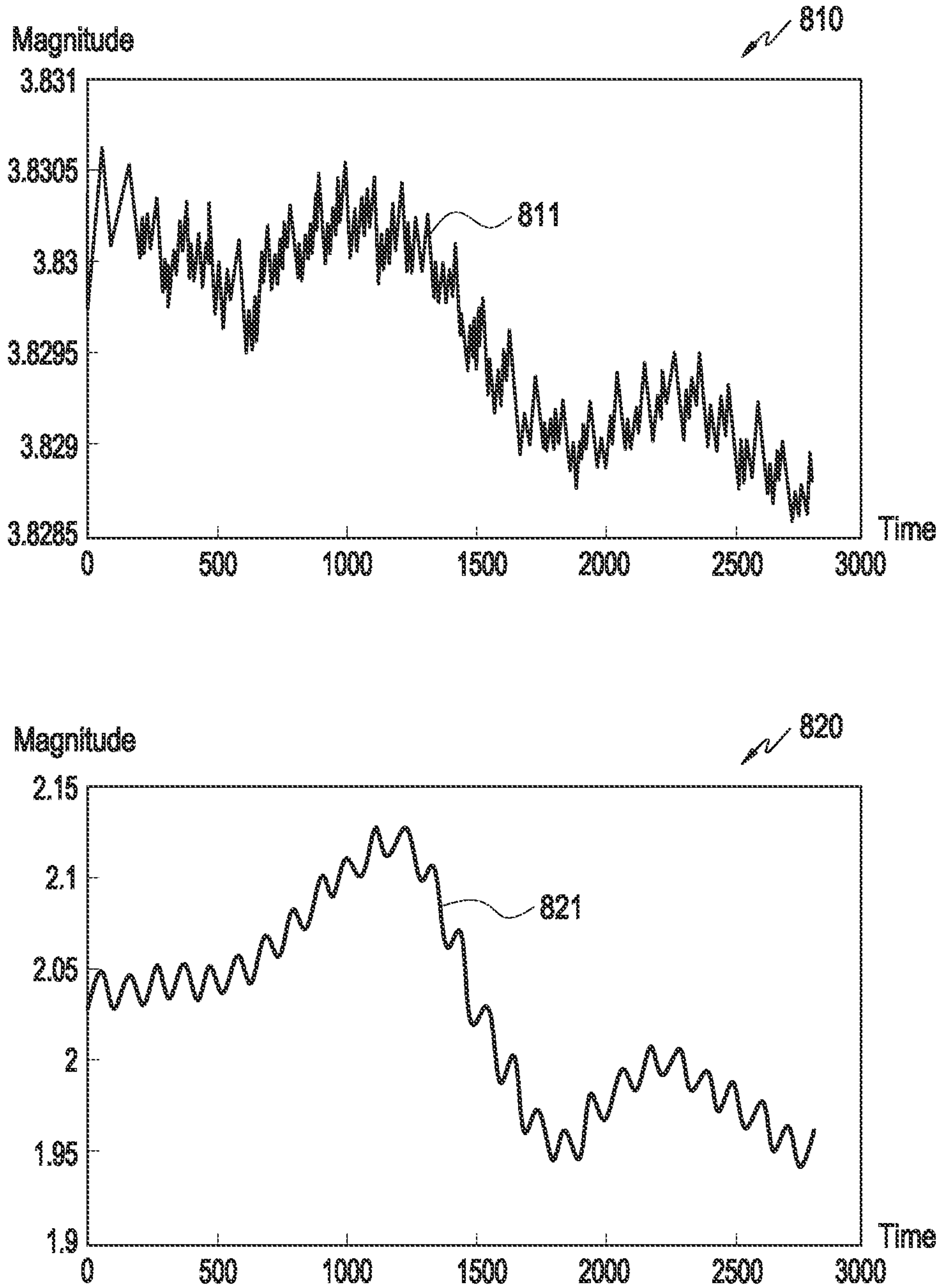
FIG. 8A is a view illustrating an example of an IR light signal and a green light signal in the time domain according to an embodiment.
Figure 8B:
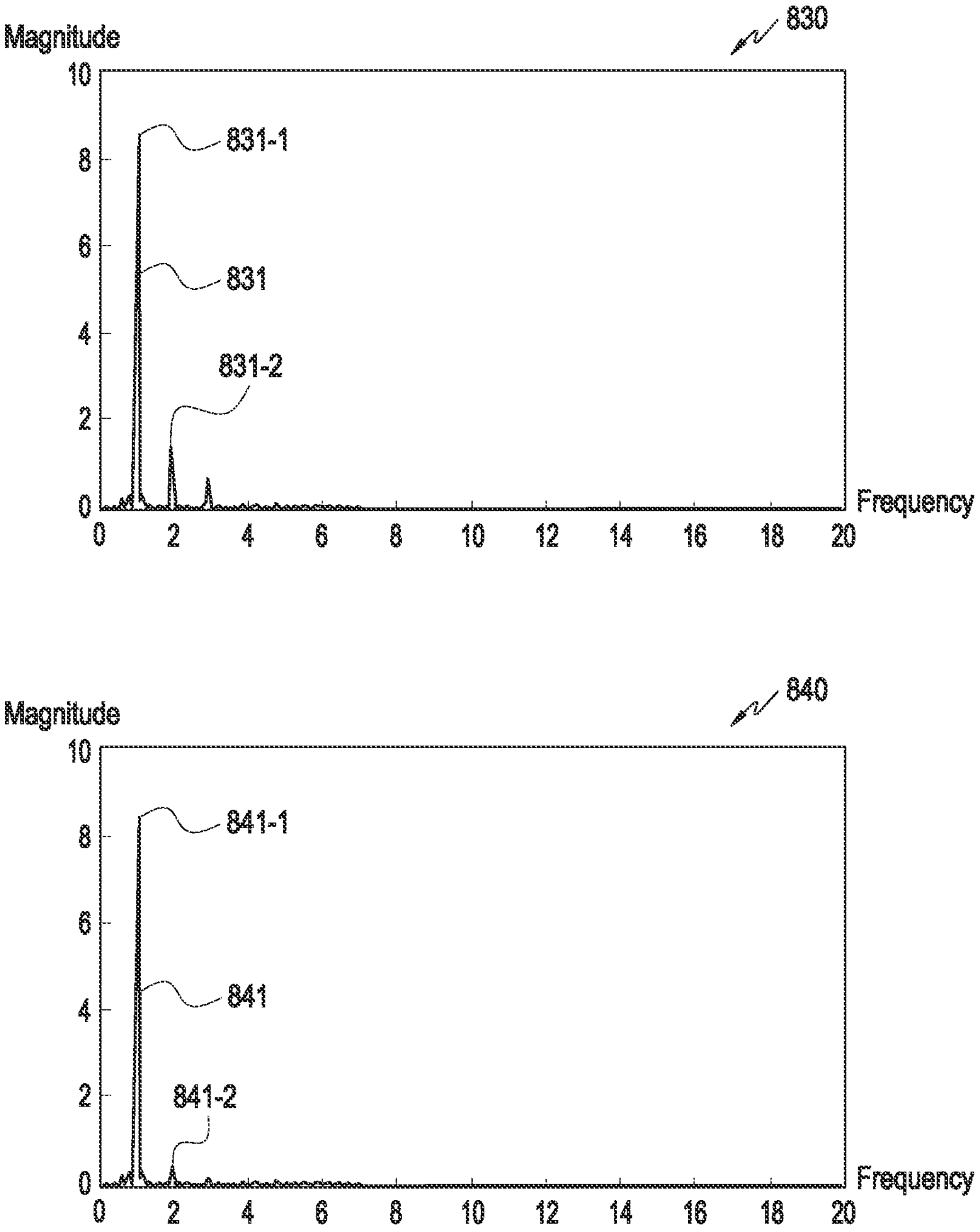
FIG. 8B is a view illustrating an example of an IR light signal and a green light signal in the frequency domain according to an embodiment.

FIG. 8A is a view illustrating an example of an IR light signal and a green light signal in the time domain according to an embodiment. FIG. 8B is a view illustrating an example of an IR light signal and a green light signal in the frequency domain according to an embodiment.

Referring to FIG. 8A, according to an embodiment, reference number 810 may be a graph representing the IR light signal 811 in the time domain, and reference number 820 may be a graph representing the green light signal 821 in the time domain. In each graph, the x axis may denote the time, and the y axis may denote the magnitude of the light signal. According to an embodiment, the processor 220 may convert the IR light signal 811 and green light signal 821 of the time domain, obtained through the PPG sensor 212, into the IR light signal 831 and green light signal 841 of the frequency domain.

Referring to FIG. 8B, according to an embodiment, reference number 830 may be a graph representing the IR light signal 831 in the frequency domain, and reference number 840 may be a graph representing the green light signal 841 in the frequency domain. In each graph, the x axis may denote the frequency, and the y axis may denote the magnitude (or power) of each light signal.

Examples of the first maximum peak frequency, second maximum peak frequency, and SNR value of each of the IR light signal 831 and the green light signal 841 of the frequency domain according to FIG. 8B may be as shown in Table 1 below.

TABLE 1

| Signal | 1$^{st}$ maximum peak frequency (Hz) | 2$^{nd}$ maximum peak frequency (Hz) | signal-to-noise ratio (SNR) |
|---|---|---|---|
| IR light signal | 0.94 | 1.88 | 5.91 |
| green light signal | 0.94 | 1.88 | 15.26 |

Referring to Table 1 above, according to an embodiment, the processor 220 may identify the state in which the SNR of the IR light signal 831 is not less than a designated value (negative number) (SNR=5.91) and may identify that the first maximum peak frequency 831-1 of the IR light signal 831 and the first maximum peak frequency 841-1 of the green light signal 841 are identical as about 0.94 Hz, the second maximum peak frequency 831-2 of the IR light signal 831 and the second maximum peak frequency 841-2 of the green light signal 841 are identical as about 1.88 Hz and, in such a case, may identify a tremorless state.

Figure 9A:
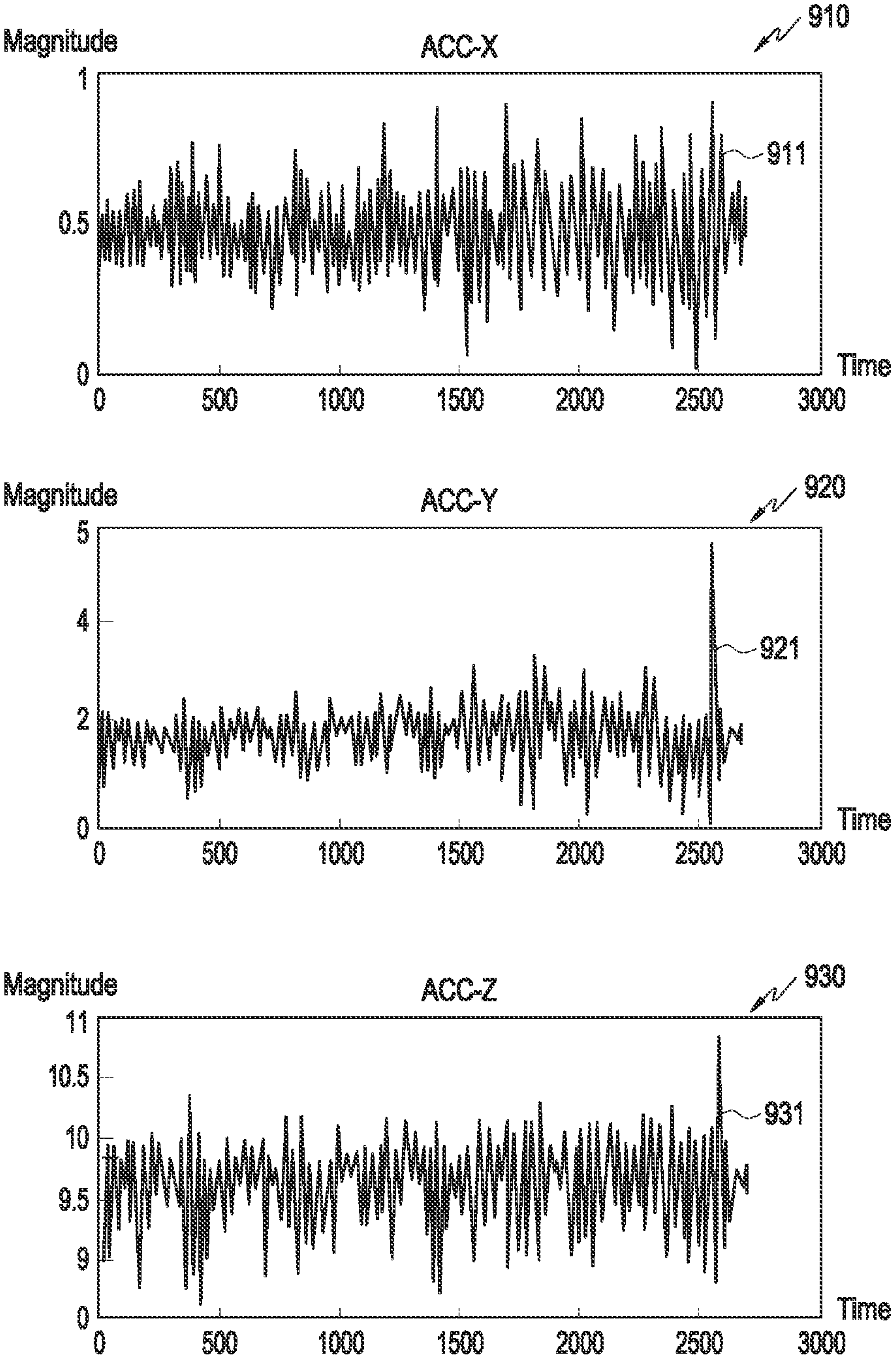
FIG. 9A is a view illustrating an example of 3-axis acceleration signals in the time domain according to an embodiment.
Figure 9B:
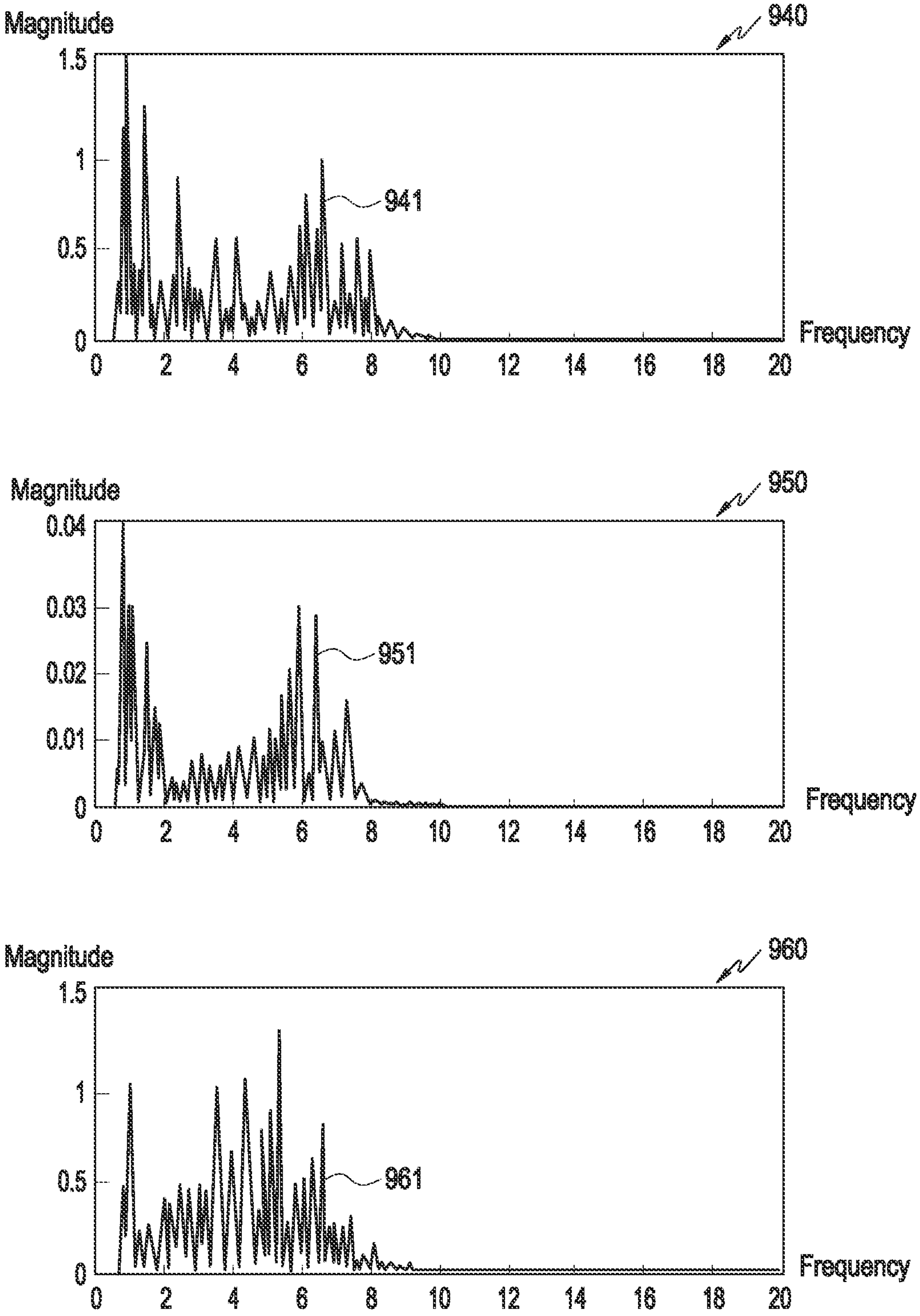
FIG. 9B is a view illustrating an example of 3-axis acceleration signals in the frequency domain according to an embodiment.

FIG. 9A is a view illustrating an example of three-axis acceleration signals in the time domain according to an embodiment. FIG. 9B is a view illustrating an example of three-axis acceleration signals in the frequency domain according to an embodiment.

Referring to FIG. 9A, according to an embodiment, reference number 910 may be a graph representing the x-axis acceleration signal 911 in the time domain, reference number 920 may be a graph representing the y-axis acceleration signal 921 in the time domain, and reference number 930 may be a graph representing the z-axis acceleration signal 931 in the time domain. In each graph, the x axis may denote the time, and the y axis may denote the magnitude of each acceleration signal. According to an embodiment, the processor 220 may convert the three-axis acceleration signals 911, 921, and 931 of the time domain, obtained through the motion sensor 214, into three-axis acceleration signals 941, 951, and 961, respectively, of the frequency domain.

Referring to FIG. 9B, according to an embodiment, reference number 940 may be a graph representing the x-axis acceleration signal 941 in the frequency domain, reference number 950 may be a graph representing the y-axis acceleration signal 951 in the frequency domain, and reference number 960 may be a graph representing the z-axis acceleration signal 961 in the frequency domain. In each graph, the x axis may denote the frequency, and the y axis may denote the magnitude of power of the acceleration signal.

According to an embodiment, the processor 220 may compare the respective first maximum peak frequencies of the three-axis acceleration signals 941, 951, and 961 of the frequency domain (e.g., the first maximum peak frequency of the x-axis acceleration signal=0.78 Hz, the first maximum peak frequency of the y-axis acceleration signal=0.70 Hz, and the first maximum peak frequency of the z-axis acceleration signal=5.22 Hz) when movement is detected through the motion sensor 214 and may compare the respective second maximum peak frequencies of the three-axis acceleration signals 941, 951, and 961 (e.g., the second maximum peak frequency of the x-axis acceleration signal=1.37 Hz, the second maximum peak frequency of the y-axis acceleration signal=0.93 Hz, and the second maximum peak frequency of the z-axis acceleration signal=0.81 Hz).

Figure 10A:
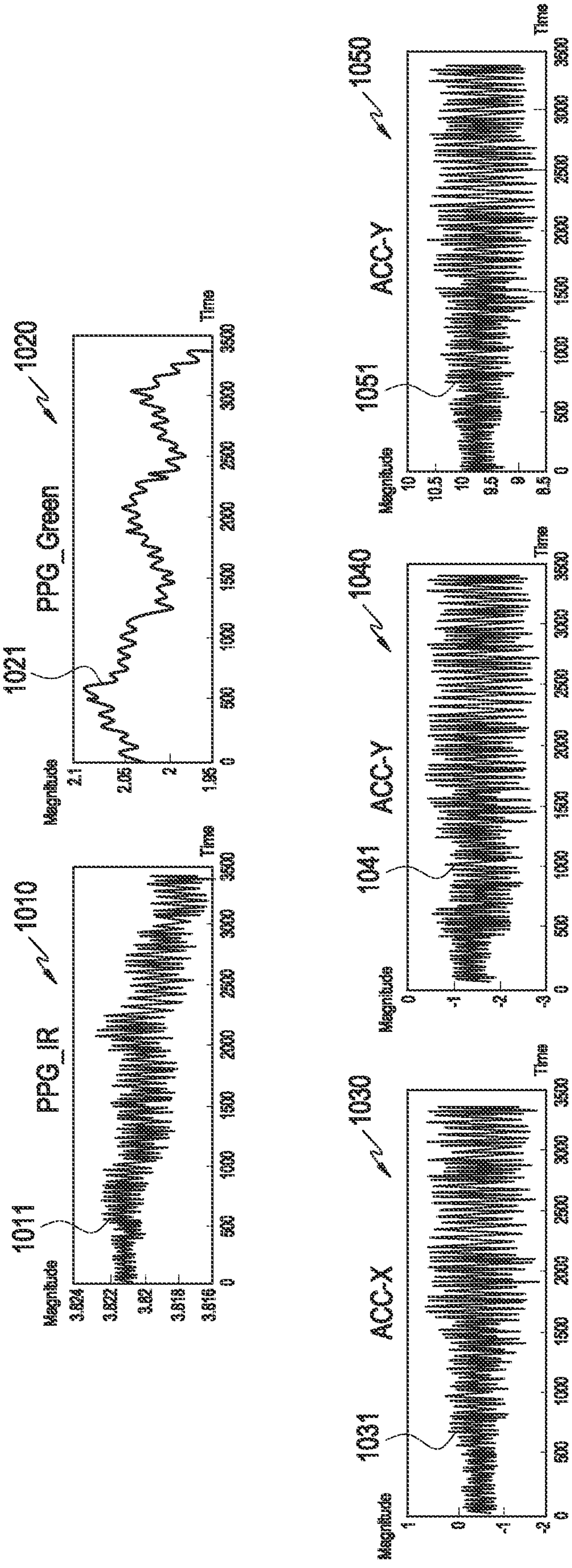
FIG. 10A is a view illustrating an IR light signal, a green light signal, an x-axis acceleration signal, a y-axis acceleration signal, and a z-axis acceleration signal in the time domain when the severity of a tremor is critical according to an embodiment.
Figure 10B:
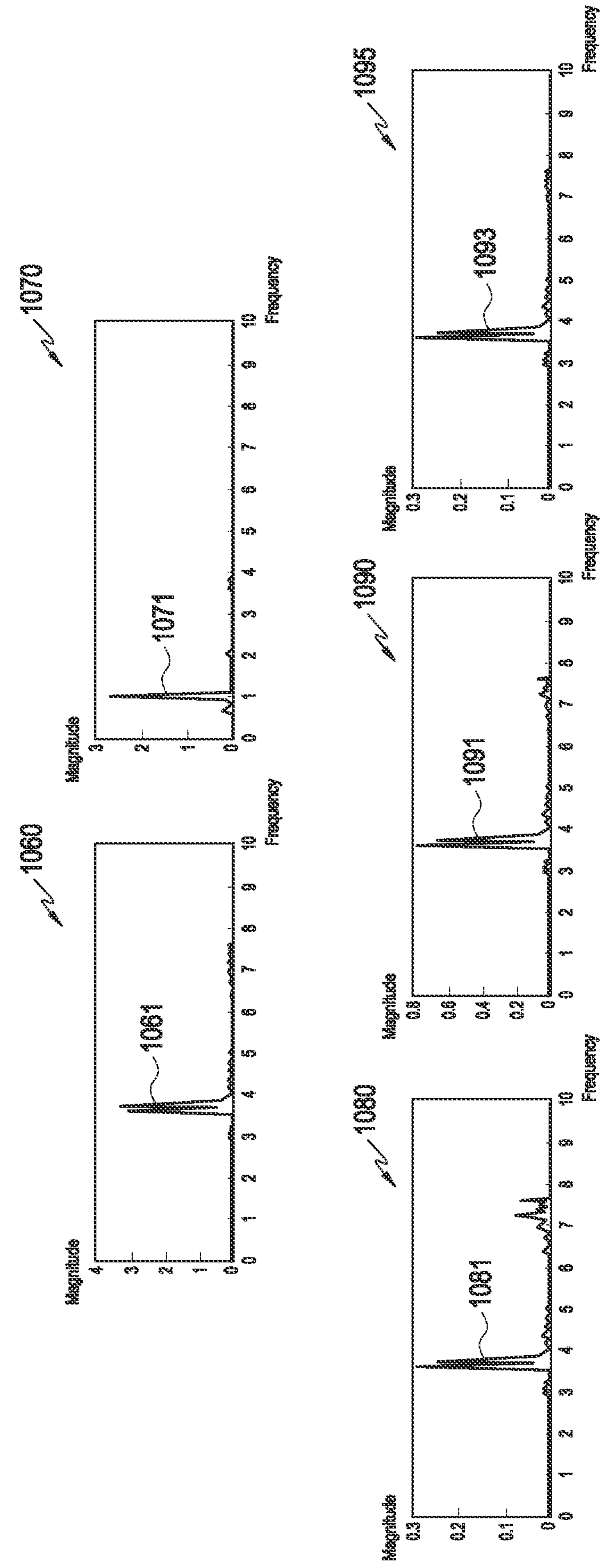
FIG. 10B is a view illustrating an IR light signal, a green light signal, an x-axis acceleration signal, a y-axis acceleration signal, and a z-axis acceleration signal in the frequency domain when the severity of a tremor is critical according to an embodiment.

FIG. 10A is a view illustrating an example of an IR light signal, a green light signal, an x-axis acceleration signal, a y-axis acceleration signal, and a z-axis acceleration signal in the time domain when the severity of tremor is critical according to an embodiment. FIG. 10B is a view illustrating an example of an IR light signal, a green light signal, an x-axis acceleration signal, a y-axis acceleration signal, and a z-axis acceleration signal in the frequency domain when the severity of tremor is critical according to an embodiment.

Referring to FIG. 10A, according to an embodiment, reference number 1010 may be a graph representing the IR light signal 1011 in the time domain, reference number 1020 may be a graph representing the green light signal 1021 in the time domain, reference number 1030 may be a graph representing the x-axis acceleration signal 1031 in the time domain, reference number 1040 may be a graph representing the y-axis acceleration signal 1041 in the time domain, and reference number 1050 may be a graph representing the z-axis acceleration signal 1051 in the time domain. In each graph, the x axis may denote the time, and the y axis may denote the frequency or the magnitude of the acceleration signal. According to an embodiment, the processor 220 may convert the IR light signal 1011, green light signal 1021, x-axis acceleration signal 1031, y-axis acceleration signal 1041, and z-axis acceleration signal 1051 of the time domain into an IR light signal, a green light signal, an x-axis acceleration signal, a y-axis acceleration signal, and a z-axis acceleration signal, respectively, of the frequency domain.

Referring to FIG. 10B, according to an embodiment, reference number 1060 may be a graph representing the IR light signal 1061 in the frequency domain, reference number 1070 may be a graph representing the green light signal 1071 in the frequency domain, reference number 1080 may be a graph representing the x-axis acceleration signal 1081 in the frequency domain, reference number 1090 may be a graph representing the y-axis acceleration signal 1091 in the frequency domain, and reference number 1095 may be a graph representing the z-axis acceleration signal 1093 in the frequency domain. In each graph, the x axis may denote the frequency, and the y axis may denote the frequency or the magnitude of the acceleration signal.

Examples of the first maximum peak frequency, second maximum peak frequency, SNR value, and tremor severity of each of the IR light signal 1061, green light signal 1071, x-axis acceleration signal 1081, y-axis acceleration signal 1091, and z-axis acceleration signal 1093 according to FIG. 10B may be as shown in Table 2 below.

TABLE 2

| Signal | $1^{st}$ maximum peak frequency (Hz) | $2^{nd}$ maximum peak frequency (Hz) | signal-to-noise ratio (SNR) | Tremor Severity |
|---|---|---|---|---|
| IR light signal (PPG_IR) | 3.8 | 3.7 | −4.89 | 3 to 4 |
| green light signal (PPG_Green) | 1.0 | 0.9 | 3.34 | |
| x-axis acceleration signal (ACC_X) | 3.7 | 3.8 | | |
| y-axis acceleration signal (ACC_Y) | 3.7 | 3.8 | | |
| z-axis acceleration signal (ACC_Z) | 3.8 | 3.6 | | |

Referring to Table 2, according to an embodiment, if there are same maximum peak frequencies, at about 3.7 Hz and about 3.8 Hz, of the three-axis acceleration signals 1081, 1091, and 1093 when the SNR of the IR light signal 1061 is less than a designated value (negative number) (SNR=−4.89), and the identical frequencies are a designated frequency (e.g., 3 Hz) or more, and the user's activity state is not a designated-activity state, the processor 220 may identify a tremorous state. According to an embodiment, the processor 220 may identify that the tremor severity is critical (e.g., 2.5<severity≤4)(e.g., 3 to 4) based on the same frequency as the first maximum peak frequency (e.g., 3.8 Hz) of the IR light signal being present in the first maximum peak frequencies of the three-axis acceleration signals 1081, 1091, and 1093 in the tremorous state (e.g., the first maximum peak frequency of z-axis acceleration signal 1093=3.8 Hz).

Figure 11A:
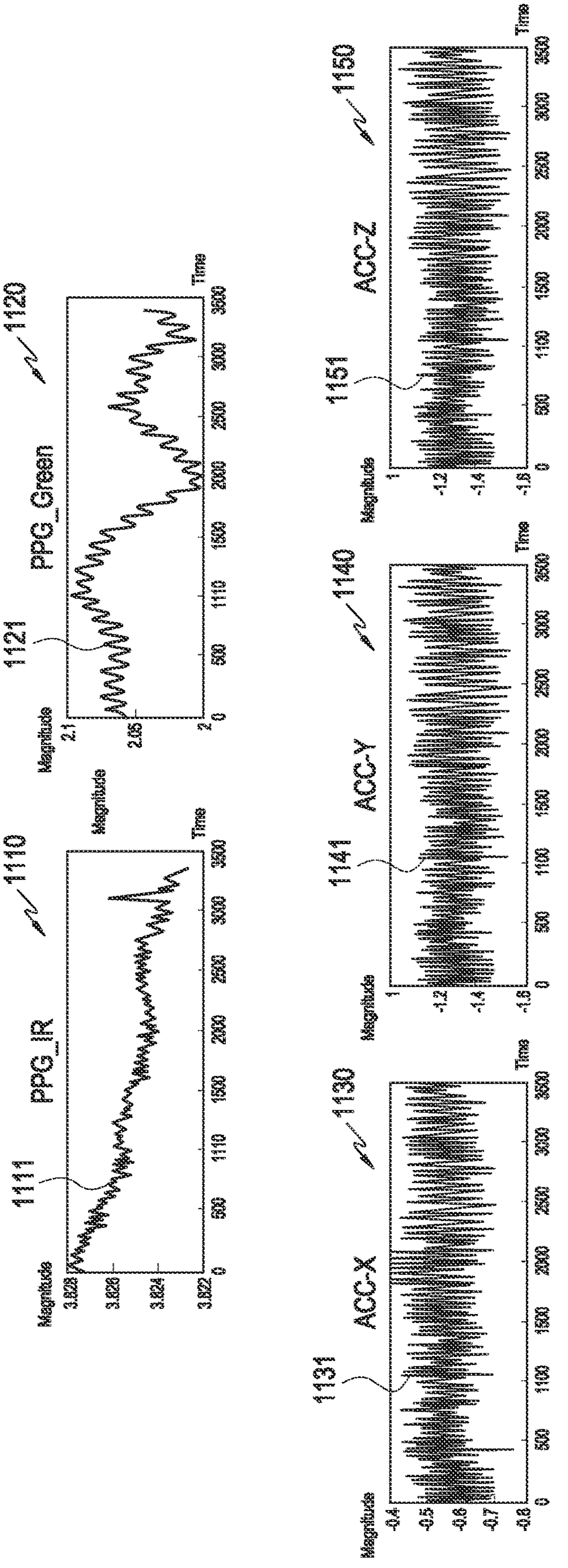
FIG. 11A is a view illustrating an IR light signal, a green light signal, an x-axis acceleration signal, a y-axis acceleration signal, and a z-axis acceleration signal in the time domain when the severity of a tremor is moderate according to an embodiment.
Figure 11B:
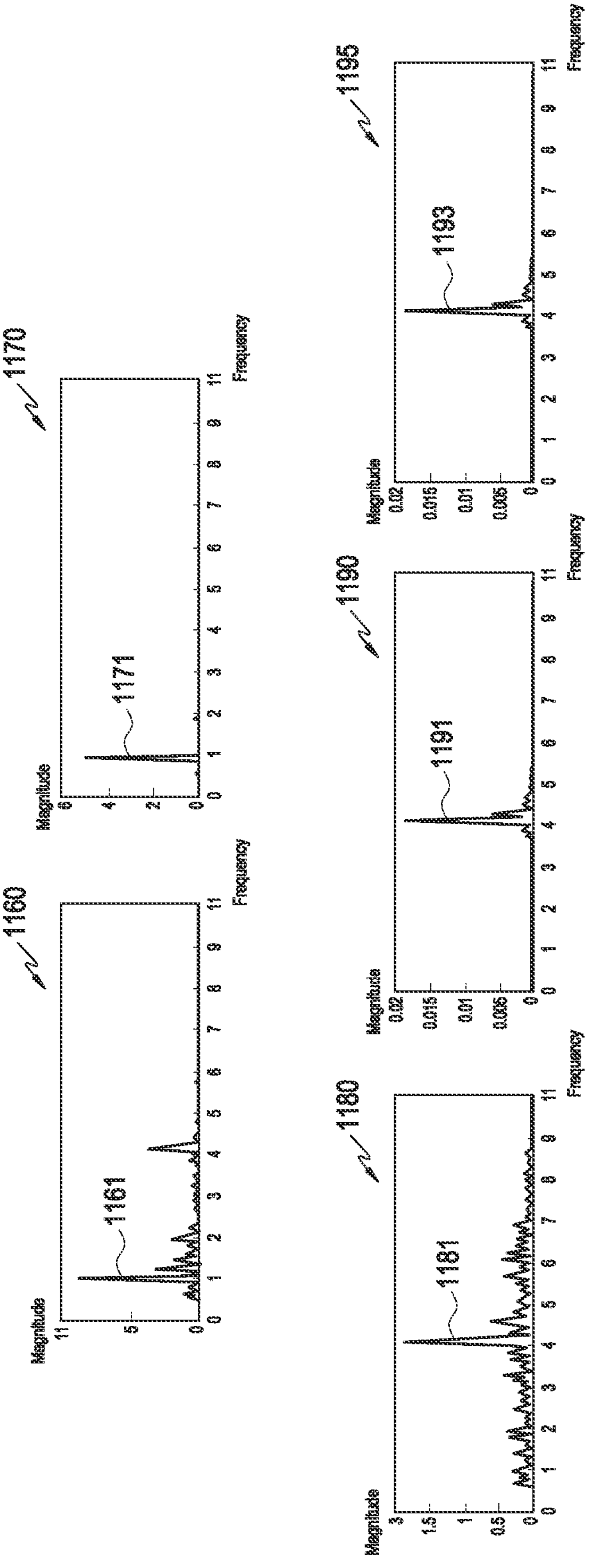
FIG. 11B is a view illustrating an IR light signal, a green light signal, an x-axis acceleration signal, a y-axis acceleration signal, and a z-axis acceleration signal in the frequency domain when the severity of a tremor is moderate according to an embodiment.

FIG. 11A is a view illustrating an example of an IR light signal, a green light signal, an x-axis acceleration signal, a y-axis acceleration signal, and a z-axis acceleration signal in the time domain when the severity of a tremor is moderate according to an embodiment. FIG. 11B is a view illustrating an example of an IR light signal, a green light signal, an x-axis acceleration signal, a y-axis acceleration signal, and a z-axis acceleration signal in the frequency domain when the severity of a tremor is moderate according to an embodiment.

Referring to FIG. 11A, according to an embodiment, reference number 1110 may be a graph representing the IR light signal 1111 in the time domain, reference number 1120 may be a graph representing the green light signal 1121 in the time domain, reference number 1130 may be a graph representing the x-axis acceleration signal 1131 in the time domain, reference number 1140 may be a graph representing the y-axis acceleration signal 1141 in the time domain, and le;2.2qreference number 1150 may be a graph representing the z-axis acceleration signal 1151 in the time domain. In each graph, the x axis may denote the time, and the y axis may denote the frequency or the magnitude of the acceleration signal. According to an embodiment, the processor 220 may convert the IR light signal 1111, green light signal 1121, x-axis acceleration signal 1131, y-axis acceleration signal 1141, and z-axis acceleration signal 1151 of the time domain into an IR light signal, a green light signal, an x-axis acceleration signal, a y-axis acceleration signal, and a z-axis acceleration signal, respectively, of the frequency domain.

Referring to FIG. 11B, according to an embodiment, reference number 1160 may be a graph representing the IR light signal 1161 in the frequency domain, reference number 1170 may be a graph representing the green light signal 1171 in the frequency domain, reference number 1180 may be a graph representing the x-axis acceleration signal 1181 in the frequency domain, reference number 1190 may be a graph representing the y-axis acceleration signal 1191 in the frequency domain, and reference number 1195 may be a graph representing the z-axis acceleration signal 1193 in the frequency domain. In each graph, the x axis may denote the frequency, and the y axis may denote the magnitude of frequency.

Examples of the first maximum peak frequency, second maximum peak frequency, SNR value, and tremor severity of each of the IR light signal 1161, green light signal 1171, x-axis acceleration signal 1181, y-axis acceleration signal 1191, and z-axis acceleration signal 1193 according to FIG. 11B may be as shown in Table 3 below.

TABLE 3

| Signal | 1st maximum peak frequency (Hz) | 2nd maximum peak frequency (Hz) | signal-to-noise ratio (SNR) | Tremor Severity |
|---|---|---|---|---|
| IR light signal (PPG_IR) | 1.0 | 1.2 | −5.85 | 2 |
| green light signal (PPG_Green) | 0.9 | 1.9 | 12.60 | |
| x-axis acceleration signal (ACC_X) | 4.1 | 4.6 | | |
| y-axis acceleration signal (ACC_Y) | 4.1 | 4.2 | | |
| z-axis acceleration signal (ACC_Z) | 4.2 | 4.1 | | |

Referring to Table 3, according to an embodiment, if there are same maximum peak frequencies, at about 4.1 Hz and about 4.2 Hz, in the three-axis acceleration signals 1181, 1191, and 1193 when the SNR of the IR light signal 11061 is less than a designated value (negative number) (SNR=−5.85), and the same maximum peak frequencies are a designated frequency (e.g., 3 Hz) or more, and the user's activity state is not a designated-activity state, the processor 220 may identify a tremorous state. According to an embodiment, the processor 220 may identify that the tremor severity is moderate (e.g., 1<severity≤2.5) (e.g., 2) based on there being at least two maximum peak frequencies, such as about 4.1 Hz and about 4.2 Hz, with the same maximum peak frequencies of the three-axis acceleration signals 1181, 1191, and 1193 in the tremorous state.

Figure 12A:
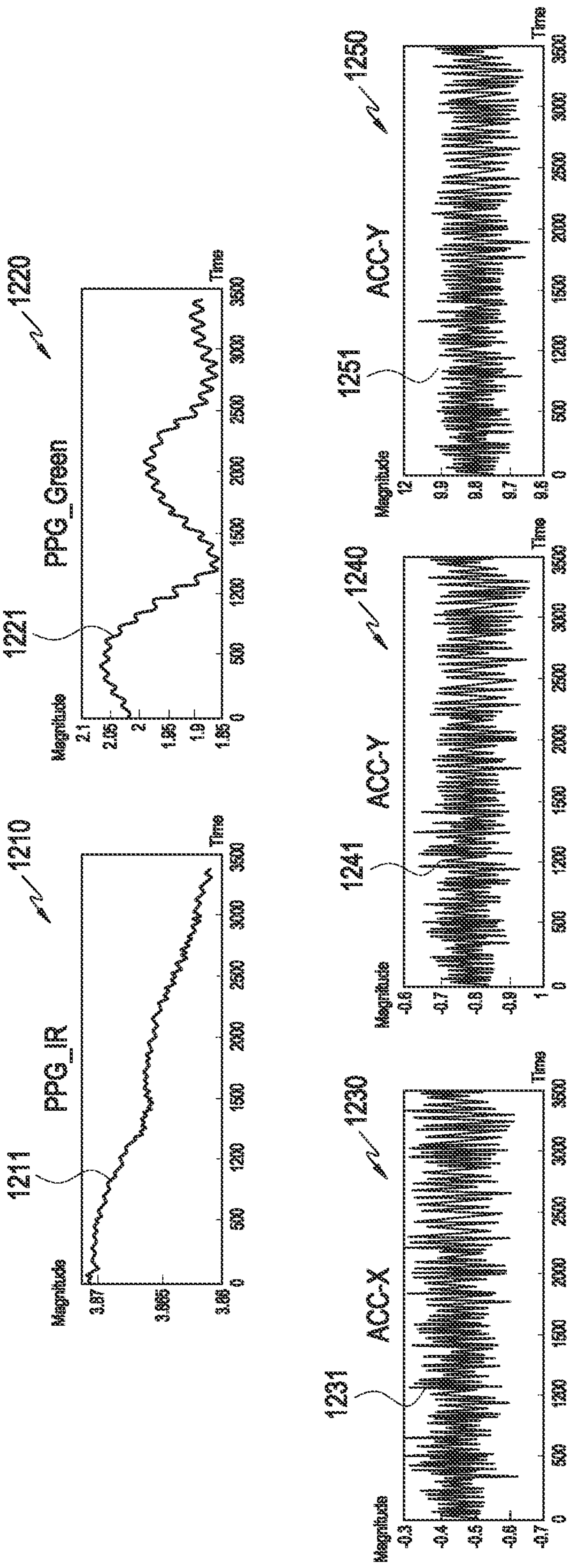
FIG. 12A is a view illustrating an IR light signal, a green light signal, an x-axis acceleration signal, a y-axis acceleration signal, and a z-axis acceleration signal in the time domain when the severity of a tremor is mild according to an embodiment.
Figure 12B:
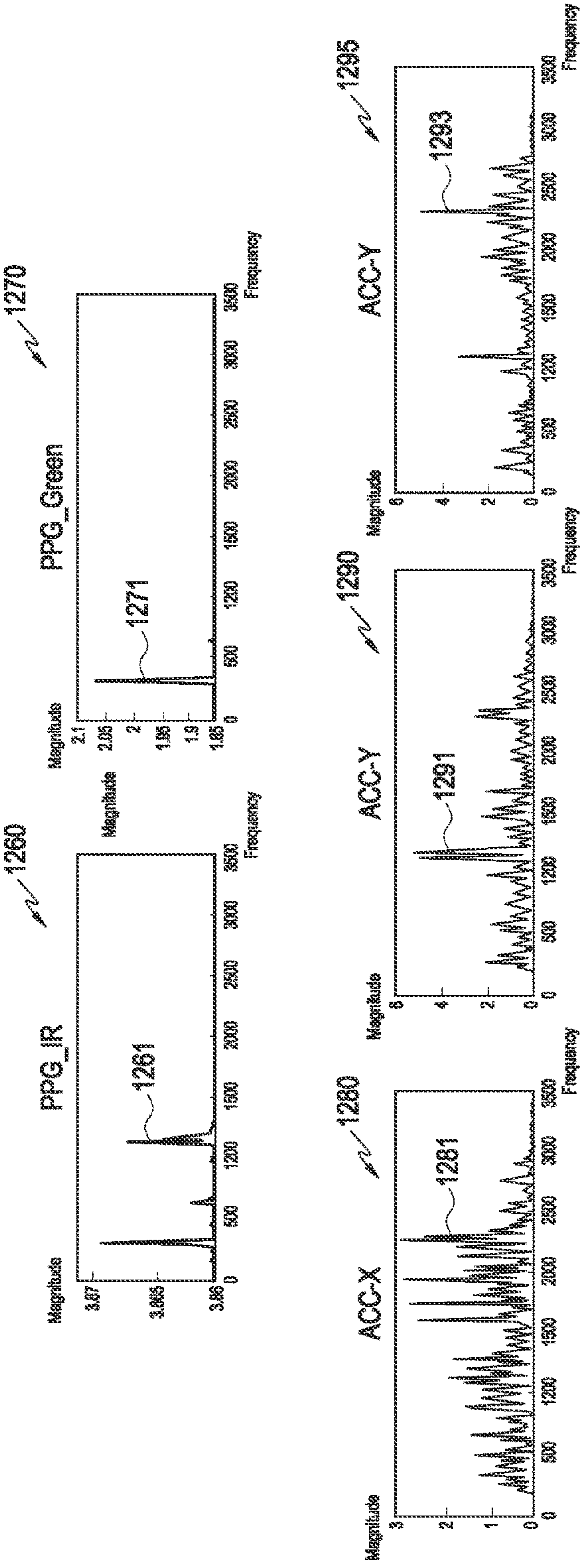
FIG. 12B is a view illustrating an IR light signal, a green light signal, an x-axis acceleration signal, a y-axis acceleration signal, and a z-axis acceleration signal in the frequency domain when the severity of a tremor is mild according to an embodiment.

FIG. 12A is a view illustrating an example of an IR light signal, a green light signal, an x-axis acceleration signal, a y-axis acceleration signal, and a z-axis acceleration signal in the time domain when the severity of a tremor is mild according to an embodiment. FIG. 12B is a view illustrating an example of an IR light signal, a green light signal, an x-axis acceleration signal, a y-axis acceleration signal, and a z-axis acceleration signal in the frequency domain when the severity of a tremor is mild according to an embodiment.

Referring to FIG. 12A, according to an embodiment, reference number 1210 may be a graph representing the IR light signal 1211 in the time domain, reference number 1220 may be a graph representing the green light signal 1221 in the time domain, reference number 1230 may be a graph representing the x-axis acceleration signal 1231 in the time domain, reference number 1240 may be a graph representing the y-axis acceleration signal 1241 in the time domain, and reference number 1250 may be a graph representing the z-axis acceleration signal 1251 in the time domain. In each graph, the x axis may denote the time, and the y axis may denote the magnitude of signal. According to an embodiment, the processor 220 may convert the IR light signal 1211, green light signal 1221, x-axis acceleration signal 1231, y-axis acceleration signal 1241, and z-axis acceleration signal 1251 of the time domain into an IR light signal, a green light signal, an x-axis acceleration signal, a y-axis acceleration signal, and a z-axis acceleration signal, respectively, of the frequency domain.

Referring to FIG. 12B, according to an embodiment, reference number 1260 may be a graph representing the IR light signal 1261 in the frequency domain, reference number 1270 may be a graph representing the green light signal 1271 in the frequency domain, reference number 1280 may be a graph representing the x-axis acceleration signal 1281 in the frequency domain, reference number 1290 may be a graph representing the y-axis acceleration signal 1291 in the frequency domain, and reference number 1295 may be a graph representing the z-axis acceleration signal 1293 in the frequency domain. In each graph, the x axis may denote the frequency, and the y axis may denote the magnitude of frequency.

Examples of the first maximum peak frequency, second maximum peak frequency, SNR value, and tremor severity of each of the IR light signal 1261, green light signal 1271, x-axis acceleration signal 1281, y-axis acceleration signal 1291, and z-axis acceleration signal 1293 according to FIG. 12B may be as shown in Table 4 below.

TABLE 4

| Signal | $1^{st}$ maximum peak frequency (Hz) | $2^{nd}$ maximum peak frequency (Hz) | signal-to-noise ratio (SNR) | Tremor Severity |
|---|---|---|---|---|
| IR light signal (PPG_IR) | 0.9 | 3.3 | −3.31 | 1 |
| green light signal (PPG_Green) | 0.9 | 1.9 | 14.13 | |
| x-axis acceleration signal (ACC_X) | 5.7 | 5.1 | | |
| y-axis acceleration signal (ACC_Y) | 3.3 | 3.4 | | |
| z-axis acceleration signal (ACC_Z) | 6.7 | 3.3 | | |

Referring to Table 4, according to an embodiment, if there are same maximum peak frequencies, at about 3.3 Hz, in the maximum peak frequencies of the three-axis acceleration signals 1281, 1291, and 1293 when the SNR of the IR light signal 1261 is less than a designated value (negative number) (SNR=−3.31), and the same maximum peak frequencies are a designated frequency (e.g., 3 Hz) or more, and the user's activity state is not a designated-activity state, the processor 220 may identify a tremorous state. According to an embodiment, the processor 220 may identify that the tremor severity is mild (e.g., 1<severity≤1) (e.g., 1) based on the first maximum peak frequency of the IR light signal 1261 and the first maximum peak frequency of the green light signal 1271 being identical, as about 0.9 Hz, in the tremorous state.

Figure 13A:
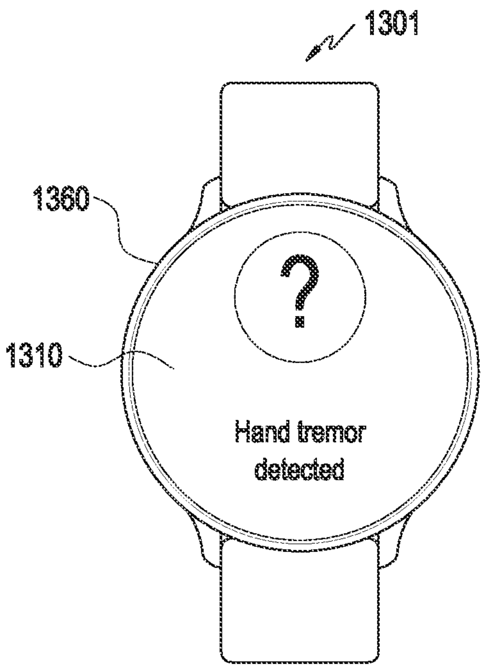
FIG. 13A is a view illustrating an example of a screen upon identifying a tremorous state in an electronic device according to an embodiment.
Figure 13B:
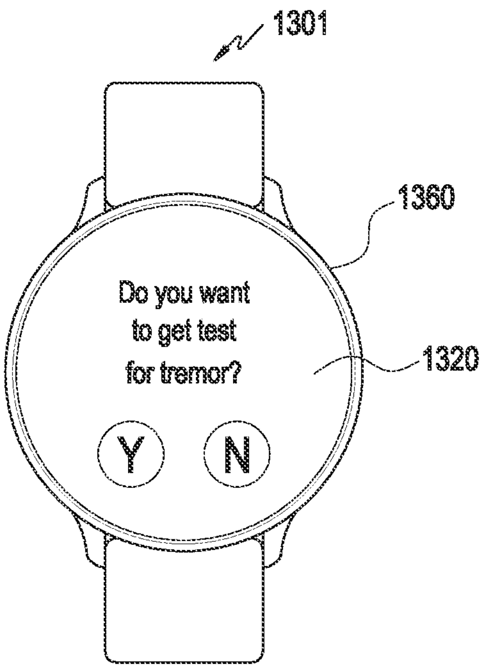
FIG. 13B is a view illustrating an example of a tremor test guide screen in an electronic device according to an embodiment.

FIG. 13A is a view illustrating an example of a screen upon identifying a tremorous state in an electronic device according to an embodiment. FIG. 13B is a view illustrating an example of a tremor test guide screen in an electronic device according to an embodiment.

Referring to FIG. 13A, according to an embodiment, a processor 220 (e.g., the processor 120 of FIG. 1) of an electronic device 1301 (e.g., the electronic device 101 of FIG. 1, the electronic device 201 of FIG. 2, or the electronic device 401 of FIG. 4) may display a tremor notification screen 1310 including a notification, such as "Hand tremor detected," on the display 1360 upon identifying a tremorous state (or upon detecting a tremor).

Referring to FIG. 13B, according to an embodiment, the processor 220 may display a tremor test selection screen 1320 for selecting whether to perform a tremor test, such as "Do you want to perform a tremor test?" on the display 1360 after displaying the tremor notification screen. According to an embodiment, if a tremor test is selected through the tremor test selection screen 1320, the processor 220 may display guide screens for a tremor test on the display 260.

Figure 14A:
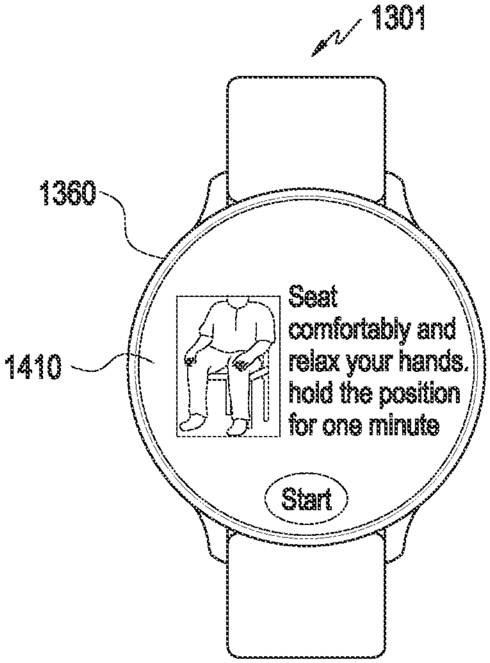
FIG. 14A is a view illustrating an example of a first guide screen for a tremor test according to an embodiment.
Figure 14B:
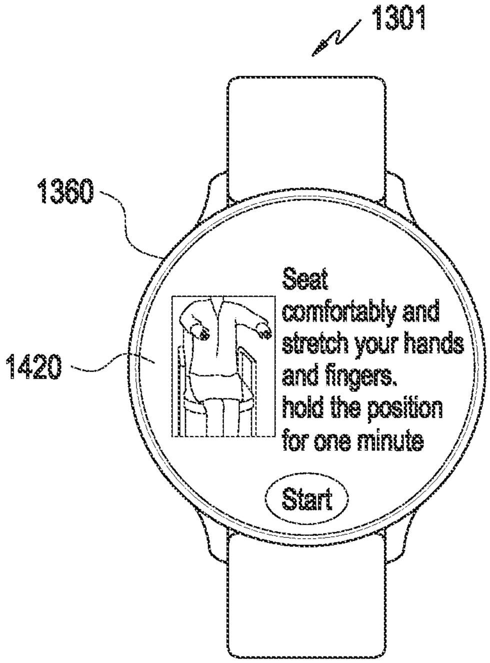
FIG. 14B is a view illustrating an example of a second guide screen for a tremor test according to an embodiment.
Figure 14C:
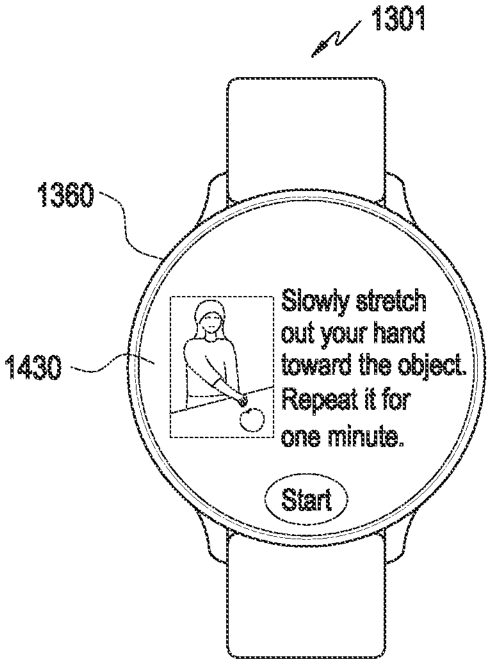
FIG. 14C is a view illustrating an example of a third guide screen for a tremor test according to an embodiment.
Figure 14D:
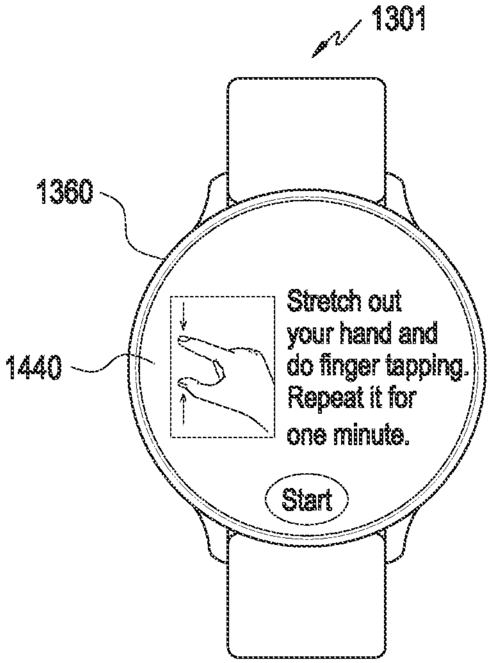
FIG. 14D is a view illustrating an example of a fourth guide screen for a tremor test according to an embodiment.

FIG. 14A is a view illustrating an example of a first guide screen for a tremor test according to an embodiment. FIG. 14B is a view illustrating an example of a second guide screen for a tremor test according to an embodiment. FIG. 14C is a view illustrating an example of a third guide screen for a tremor test according to an embodiment. FIG. 14D is a view illustrating an example of a fourth guide screen for a tremor test according to an embodiment.

Referring to FIG. 14A, according to an embodiment, the processor 220 of the electronic device 1301 may display, on the display 1360, a first guide screen 1410 to test whether a tremor is identified (detected or sensed) in a first position in which the user sits comfortably with his hands relaxed, based on a tremor test request (or selection) from the user. For example, the first guide screen 1410 may include all or some of an image for guiding to the first position for a tremor test, a message for guiding to the first position for a tremor test (e.g., "Sit comfortably. Relax your hands. Hold the position for one minute") and a start button (or icon) for starting the test. According to an embodiment, the processor 220 may perform a tremor detection operation (e.g., at least some of the operations of FIGS. 5, 6, and 7) in the first position based on the user's start button input. According to an embodiment, after performing the tremor detection operation in the first position, the processor 220 may identify the severity of the tremor, provide it, or provide a message for recommending a hospital visit.

Referring to FIG. 14B, according to an embodiment, the processor 220 of the electronic device 1301 may display, on the display 1360, a second guide screen 1420 to test whether a tremor is identified (detected or sensed) in a second position in which the user sits comfortable with his hands and fingers stretched forward, based on a tremor test request (or selection) from the user. For example, the second guide screen 1420 may include all or, at least some of an image for guiding to the second position for a tremor test, a message for guiding to the second position for a tremor test (e.g., "Sit comfortably. Stretch out your hands and fingers. Hold the position for one minute") and a start button (or icon) for starting the test. According to an embodiment, the processor 220 may perform a tremor detection operation (e.g., at least some or all of the operations of FIGS. 5, 6, and 7) in the second position based on the user's start button input. According to an embodiment, after performing the tremor detection operation in the second position, the processor 220 may identify the severity of the tremor, provide it, or provide a message for recommending a hospital visit.

Referring to FIG. 14C, according to an embodiment, the processor 220 of the electronic device 1301 may display, on the display 1360, a third guide screen 1430 to test whether a tremor is identified (detected or sensed) in a third position in which the user slowly stretches his hands toward an object, based on a tremor test request (or selection) from the user. For example, the third guide screen 1430 may include all or, at least some of an image for guiding to the third position for a tremor test, a message for guiding to the third position for a tremor test (e.g., "Slowly stretch out your hand toward the object. Repeat it for one minute") and a start button (or icon) for starting the test. According to an embodiment, the processor 220 may perform a tremor detection operation (e.g., at least some of the operations of FIGS. 5, 6, and 7) in the third position based on the user's start button input. According to an embodiment, after performing the tremor detection operation in the third position, the processor 220 may identify the severity of the tremor, provide it, or provide a message for recommending a hospital visit.

Referring to FIG. 14D, according to an embodiment, the processor 220 of the electronic device 1301 may display, on the display 1360, a fourth guide screen 1440 to test whether a tremor is identified (detected or sensed) in a fourth position in which the user stretches his hand forward and does finger-tapping, based on a tremor test request (or selection) from the user. For example, the fourth guide screen 1440 may include all or, at least some of an image for guiding to the fourth position for a tremor test, a message for guiding to the user's fourth position for a tremor test (e.g., "Stretch out your hand and do finger-tapping. Repeat it for one minute") and a start button (or icon) for starting the test. According to an embodiment, the processor 220 may perform a tremor detection operation (e.g., at least some of the operations of FIGS. 5, 6, and 7) in the fourth position based on the user's start button input. According to an embodiment, after performing the tremor detection operation in the fourth position, the processor 220 may identify the severity of the tremor, provide it, or provide a message for recommending a hospital visit.

According to an embodiment, the processor 220 may further display a screen for a tremor test for each of one or more other positions than the first to fourth positions and may further perform a tremor detection operation on each of the other positions. According to an embodiment, the first to fourth positions are examples and any other positions are also possible as long as a tremor test is possible in those positions.

Figure 15:
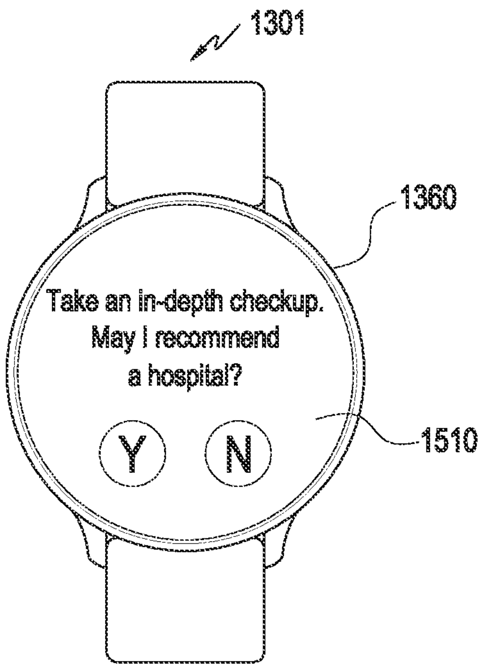
FIG. 15 is a view illustrating an example of a hospital-linked service screen based on a result of tremor detection in an electronic device according to an embodiment.

FIG. 15 is a view illustrating an example of a hospital-linked service screen based on a result of tremor detection in an electronic device according to an embodiment.

Referring to FIG. 15, according to an embodiment, the processor 220 of the electronic device 1301 may display, on the display 1360, a hospital visit recommendation message 1510 (e.g., Go to the hospital to take an in-depth checkup. May I recommend a hospital?) if a result of tremor detection shows a tremorous state. According to an embodiment, the processor 220 may display information about the hospital or communicate with an associated hospital based on the user's input on the accept (Y) button.

The electronic device according to various embodiments may be one of various types of electronic devices. The electronic devices may include, for example, a portable communication device (e.g., a smart phone), a computer device, a portable multimedia device, a portable medical device, a camera, a wearable device, or a home appliance. According to an embodiment of the disclosure, the electronic devices are not limited to those described above.

It should be appreciated that various embodiments of the present disclosure and the terms used therein are not intended to limit the technological features set forth herein to particular embodiments and include various changes, equivalents, or replacements for a corresponding embodiment. With regard to the description of the drawings, similar reference numerals may be used to refer to similar or related elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "1st" and "2nd," or "first" and "second" may be used to simply distinguish a corresponding component from another, and does not limit the components in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), it means that the element may be coupled with the other element directly (e.g., wiredly), wirelessly, or via a third element.

As used herein, the term "module" may include a unit implemented in hardware, software, or firmware, and may interchangeably be used with other terms, for example, "logic," "logic block," "part," or "circuitry". A module may be a single integral component, or a minimum unit or part thereof, adapted to perform one or more functions. For example, according to an embodiment, the module may be implemented in a form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code generated by a compiler or a code executable by an interpreter. The machine-readable storage medium may be provided in the form of a non-transitory storage medium. Wherein, the term "non-transitory" simply means that the storage medium is a tangible device, and does not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program products may be traded as commodities between sellers and buyers. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each component (e.g., a module or a program) of the above-described components may include a single entity or multiple entities. According to various embodiments, one or more of the above-described components may be omitted, or one or more other components may be added. Alternatively or additionally, a plurality of components (e.g., modules or programs) may be integrated into a single component. In such a case, according to various embodiments, the integrated component may still perform one or more functions of each of the plurality of components in the same or similar manner as they are performed by a corresponding one of the plurality of components before the integration. According to various embodiments, operations performed by the module, the program, or another component may be carried out sequentially, in parallel, repeatedly, or heuristically, or one or more of the operations may be executed in a different order or omitted, or one or more other operations may be added.

According to certain embodiments, there may be provided a non-volatile storage medium storing instructions configured to, when executed by an electronic device, cause the electronic device to perform at least one operation. The at least one operation may comprise obtaining a first light signal and a second light signal sensed by a PPG sensor and three-axis acceleration signals sensed by a motion sensor, identifying a tremorous state using the first light signal, the second light signal, and the three-axis acceleration signals, and displaying information indicating the tremorous state on a display.

Certain of the above-described embodiments of the present disclosure can be implemented in hardware, firmware or via the execution of software or computer code that can be stored in a recording medium such as a CD ROM, a Digital Versatile Disc (DVD), a magnetic tape, a RAM, a floppy disk, a hard disk, or a magneto-optical disk or computer code downloaded over a network originally stored on a remote recording medium or a non-transitory machine readable medium and to be stored on a local recording medium, so that the methods described herein can be rendered via such software that is stored on the recording medium using a general purpose computer, or a special processor or in programmable or dedicated hardware, such as an ASIC or FPGA. As would be understood in the art, the computer, the processor, microprocessor controller or the programmable hardware include memory components, e.g., RAM, ROM, Flash, etc. that may store or receive software or computer code that when accessed and executed by the computer, processor or hardware implement the processing methods described herein.

The embodiments herein are provided merely for better understanding of the present invention, and the present invention should not be limited thereto or thereby. It should be appreciated by one of ordinary skill in the art that various changes in form or detail may be made to the embodiments without departing from the scope of the present invention defined by the following claims.

What is claimed is:

1. An electronic device comprising,
communication circuitry;
a display;
a photoplethysmography (PPG) sensor;
a motion sensor;
memory storing instructions; and
at least one processor,
wherein the instructions, when executed by the at least one processor collectively or individually, cause the electronic device to:
obtain a first light signal and a second light signal sensed by the PPG sensor and acceleration signals sensed by the motion sensor, wherein the first light signal includes more motion-induced noise components than the second light signal, wherein the first light signal includes an infrared (IR) signal, the second light signal includes a green light signal, and the acceleration signals include three-axis acceleration signals,
identify a tremor state of a user wearing the electronic device using the first light signal, the second light signal, a comparison of the first light signal and the second light signal, and a comparison among the acceleration signals, wherein the tremor state is identified when a signal-to-noise ratio (SNR) value of the IR light signal is greater than a designated value, a first maximum peak frequency and a second maximum peak frequency of the IR light signal are different from a first maximum peak frequency and a second maximum peak frequency of the green light signal, there are identical frequencies in maximum peak frequencies of the three-axis acceleration signals, the identical frequencies are a designated frequency or more, and a user's activity state is not a designated-activity state,
display a guide screen for performing a tremor test, and perform the tremor test based on a request of the user.

2. The electronic device of claim 1, wherein the instructions, when executed by the at least one processor collectively or individually, cause the electronic device to identify a severity level of the tremor state through performing the tremor test.

3. The electronic device of claim 1, wherein the instructions, when executed by the at least one processor collectively or individually, cause the electronic device to transmit information indicating the tremor state through the communication circuitry to an external electronic device.

4. The electronic device of claim 1,
wherein the first light signal includes an infrared (IR) signal, the second light signal includes a green light signal, and the acceleration signals include three-axis acceleration signals, and
wherein the instructions, when executed by the at least one processor collectively or individually, cause the electronic device to:
identify the tremor state when a signal-to-noise ratio (SNR) value of the IR light signal is less than a designated value, there are identical frequencies in maximum peak frequencies of the three-axis acceleration signals, the identical frequencies are a designated frequency or more, and a user's activity state is not a designated-activity state.

5. The electronic device of claim 4, wherein the designated frequency is 3 Hz.

6. The electronic device of claim 4, wherein the instructions, when executed by the at least one processor collectively or individually, cause the electronic device to:
identify a tremorless state based on the SNR value of the IR light signal being greater than the designated value, and a first maximum peak frequency and a second maximum peak frequency of the IR light signal being identical to a first maximum peak frequency and a second maximum peak frequency of the green light signal.

7. The electronic device of claim 4, wherein the instructions, when executed by the at least one processor collectively or individually, cause the electronic device to:
identify a voluntarily active state when the identical frequencies are absent, or when the identical frequencies are less than the designated frequency, or when the user's activity state is the designated-activity state.

8. The electronic device of claim 1, wherein the instructions, when executed by the at least one processor collectively or individually, cause the electronic device to display, on the display, a hospital associated service screen based on identifying the tremor state.

9. A method for detecting a tremor of a user wearing an electronic device, the method comprising:
obtaining a first light signal and a second light signal sensed by a PPG sensor and acceleration signals sensed by a motion sensor, wherein the first light signal includes more motion-induced noise components than the second light signal, wherein the first light signal includes an infrared (IR) signal, the second light signal includes a green light signal, and the acceleration signals include three-axis acceleration signals;

identifying a tremor state of a user wearing the electronic device using the first light signal, the second light signal, a comparison of the first light signal and the second light signal, and a comparison among the acceleration signals, wherein the tremor state is identified when a signal-to-noise ratio (SNR) value of the IR light signal is greater than a designated value, a first maximum peak frequency and a second maximum peak frequency of the IR light signal are different from a first maximum peak frequency and a second maximum peak frequency of the green light signal, there are identical frequencies in maximum peak frequencies of the three-axis acceleration signals, the identical frequencies are a designated frequency or more, and a user's activity state is not a designated-activity state;

displaying a guide screen for performing a tremor test; and performing the tremor test based on a request of the user.

10. The method of claim 9, further comprising identifying a severity level of the tremor state through the performing of the tremor test.

11. The method of claim 9, further comprising transmitting information indicating the tremor state to an external electronic device through communication circuitry of the electronic device.

12. The method of claim 9, wherein the first light signal includes an infrared (IR) signal, the second light signal includes a green light signal, and the acceleration signals include three-axis acceleration signals, and further comprising identifying the tremor state when a signal-to-noise ratio (SNR) value of the IR light signal is greater than a designated value, a first maximum peak frequency and a second maximum peak frequency of the IR light signal are different from a first maximum peak frequency and a second maximum peak frequency of the green light signal, there are identical frequencies in maximum peak frequencies of the three-axis acceleration signals, the identical frequencies are a designated frequency or more, and a user's activity state is not a designated-activity state.

13. The method of claim 9, further comprising identifying a tremorless state based on the SNR value of the IR light signal being greater than the designated value, and a first maximum peak frequency and a second maximum peak frequency of the IR light signal being identical to a first maximum peak frequency and a second maximum peak frequency of the green light signal.

14. The method of claim 9, further comprising identifying a voluntarily active state when the identical frequencies are absent, or when the identical frequencies are less than the designated frequency, or when the user's activity state is the designated-activity state.

15. The method of claim 9, further comprising displaying, on a display, a hospital associated service screen based on identifying the tremor state.

16. A non-volatile storage medium storing instructions, wherein the instructions are configured to, when executed by an electronic device, cause the electronic device to perform at least one operation, the at least one operation comprising:

obtaining a first light signal and a second light signal sensed by a PPG sensor and acceleration signals sensed by a motion sensor, wherein the first light signal includes more motion-induced noise components than the second light signal, wherein the first light signal includes an infrared (IR) signal, the second light signal includes a green light signal, and the acceleration signals include three-axis acceleration signals;

identifying a tremor state of a user wearing the electronic device using the first light signal, the second light signal, a comparison of the first light signal and the second light signal, and a comparison among the acceleration signals, wherein the tremor state is identified when a signal-to-noise ratio (SNR) value of the IR light signal is greater than a designated value, a first maximum peak frequency and a second maximum peak frequency of the IR light signal are different from a first maximum peak frequency and a second maximum peak frequency of the green light signal, there are identical frequencies in maximum peak frequencies of the three-axis acceleration signals, the identical frequencies are a designated frequency or more, and a user's activity state is not a designated-activity state;

displaying a guide screen for performing a tremor test; and performing the tremor test based on request of the user.

* * * * *